US 8,455,211 B2
Jun. 4, 2013

(12) United States Patent
Dimitrov et al.

(10) Patent No.: US 8,455,211 B2
(45) Date of Patent: Jun. 4, 2013

(54) *ANAPLASMA* TRANSLOCATED SUBSTRATE-1 (ATS-1) AND SERO-DETECTION OF *ANAPLASMA PHAGOCYTOPHILUM*

(75) Inventors: Denise Dimitrov, Hamilton, NJ (US); John G. Hoey, Framingham, MA (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/134,980

(22) Filed: Jun. 22, 2011

(65) Prior Publication Data

US 2012/0088256 A1   Apr. 12, 2012

Related U.S. Application Data

(60) Provisional application No. 61/399,639, filed on Jul. 15, 2010.

(51) Int. Cl.
*G01N 33/569* (2006.01)
*C07H 21/00* (2006.01)

(52) U.S. Cl.
USPC .......................... 435/7.32; 435/7.92; 422/430

(58) Field of Classification Search
None
See application file for complete search history.

(56) References Cited

U.S. PATENT DOCUMENTS 6,964,855 B2   11/2005   O'Connor
7,304,139 B2   12/2007   Alleman

OTHER PUBLICATIONS

Ehrlichiosis and Anaplasmosis. 2008 Case Definition. http://www.cdc.gov/osels/ph_surveillance/nndss/print/ehrlichiosis_2008.htm Retrieved Sep. 6, 2012.*
Bakken, J.S., et al, JAMA, Jul. 20, 1994, 272(3): 212-218.
Chang, A.C., et al, Nature, Oct. 19, 1978, 275(5681): 617-624.
Deutscher, M.P., Methods Enzymol, 1990, 182:779-80.
Goeddel, D.V., Nucleic Acids Research, 1980, 4057-4074, vol. 8—Issue 18.
Goeddel, D.V., Methods Enzymol, 1990, 185:3-7.
Jones, E.W., Genetics, Jan. 1977, 85:22-33.
Keown, W.A., Methods Enzymol, 1990, 185:527-537.
Magnarelli, L.A., et al, Journal of Wildlife Diseases, 2004, 40(2): 249-258.
Niu, Hua, et al, PLoS Pathogens, Feb. 19, 2010,vol. 6—Issue 2, 1-18.
O'Sullivan, M.J., et al, Methods Enzymol, 1981, 73(Pt B):147-166.
Park, J., et al, Clinical and Diagnostic Laboratory Immunology, Nov. 2003, 1059-1064.
Stinchcomb, D.T., et al, Nature, Nov. 1, 1979, 282(5734): 39-43.
Thomas, P.S., Proc. Natl. Acad. Sct. USA, Sep. 1980, vol. 77, No. 9, 5201-5205.
Urlaub, G., et al, Natl. Acad. Sct. USA, Jul. 1980, vol. 77, No. 7, 4216-4220.
Van Der Eb, et al, Gene, 1977, 2:(3-4):115-132.
Van Solingen, P., et al, Journal of Bacteriology, May 1977, vol. 130, No. 2, 946-947.
Varde, S., et al, Emerging Infectious Diseases, Jan. 1998, vol. 4, No. 1, 97-99.
Zhi, N., et al, Journal of CLinical Microbiology, Jun. 1988, vol. 36, No. 6, 1666-1673.

* cited by examiner

*Primary Examiner* — Oluwatosin Ogunbiyi
(74) *Attorney, Agent, or Firm* — Siu K. Lo

(57) ABSTRACT

Disclosed is the use of isolated Ats-1 protein in *Anaplasma phagocytophilum* in the ELISA detection of *Anaplasma* pathogen. The recombinant expression of Ats-1 and its use as a kit for ELISA are also disclosed.

20 Claims, 16 Drawing Sheets

Figure 1

Nucleotide Sequence for Ats-1 (SEQ ID No: 1)

```
   1 atgctaataa gaagaattct gactacatct aggaacgtcg ctgcgcgcat tgtttctgga
  61 ttcacagctc cagccactga aaatactagc gcgagaacct caagaaatct cttaggtaca
 121 acaggaaatt tctttaatgg cctcatgggt aaaggaaagc cttttacca tcgcgcttct
 181 gagatgcaga atctcccctg ggataaagag aggggcacaa aaataagttc gcactatgct
 241 caaacagggc agttggtact gcaaattggc gatggaaggg tatctgaagg cgccttacag
 301 atgttagaag cactggataa tagtgacgta ggagaactag atccaagtag taaaggttta
 361 aatccaggaa tggatattgg cgccagaatg gatcataacc gagctaaaaa cgagtgtggt
 421 gcgcttttag atcttagaaa aaagctggaa gaaacaggtg gtaagatttc cgtagagcgc
 481 acaggcgacg gcttcactag aatgctagtg ataaaaatag acacaaaaaa taaatcagag
 541 gaagaggtag aaaaagaagt acaactggta ctgggcactc taggtgttgg aagtaaaata
 601 ctggccaagt ccattgctaa agagctaatg caccaagcaa aaacaaaaga tatgaatgct
 661 cttgctccag taagccatac tcctcctgca caatcaaaac ctgacagtga tattcaagaa
 721 aatagtgaaa atctgcatc agcagacgct aaaaatagat ctcaggcacc tgatcaagaa
 781 gaaaattcac cccgtgatac aacccgcaga aactctacta caaatggaga agaacgcatt
 841 ttctcattga gcggagatgc gtcacctagc agaccttctt caggtgcagg caccgatcag
 901 gccgttcagc aagcacactt cctaagagac tcagaggatc gtgtgcatgg cagcagcggt
 961 atcaccaacc aaggagcagc ggctatgcaa caagcggtgc tttctgctgc tagaggacta
1021 agcgatgttt ctcatgatga ttcagcacaa acacaaggga atcctactgt cactcctta
1081 gtaagcgcac agaatagagg cccagaaaca catggtaaag gtacgaggta a
```

Figure 2

Amino Acid Sequence for Ats-1 (SEQ ID No: 2)

MetLeuIleArgArgIleLeuThrThrSerArgAsnValAlaAlaArgIleValSerGly

PheThrAlaProAlaThrGluAsnThrSerAlaArgThrSerArgAsnLeuLeuGlyThr

ThrGlyAsnPhePheAsnGlyLeuMetGlyLysGlyLysProPheTyrHisArgAlaSer

GluMetGlnAsnLeuProTrpAspLysGluArgGlyThrLysIleSerSerHisTyrAla

GlnThrGlyGlnLeuValLeuGlnIleGlyAspGlyArgValSerGluGlyAlaLeuGln

MetLeuGluAlaLeuAspAsnSerAspValGlyGluLeuAspProSerSerLysGlyLeu

AsnProGlyMetAspIleGlyAlaArgMetAspHisAsnArgAlaLysAsnGluCysGly

AlaLeuLeuAspLeuArgLysLysLeuGluGluThrGlyGlyLysIleSerValGluArg

ThrGlyAspGlyPheThrArgMetLeuValIleLysIleAspThrLysAsnLysSerGlu

GluGluValGluLysGluValGlnLeuValLeuGlyThrLeuGlyValGlySerLysIle

LeuAlaLysSerIleAlaLysGluLeuMetHisGlnAlaLysThrLysAspMetAsnAla

LeuAlaProValSerHisThrProProAlaGlnSerLysProAspSerAspIleGlnGlu

AsnSerGluLysSerAlaSerAlaAspAlaLysAsnArgSerGlnAlaProAspGlnGlu

GluAsnSerProArgAspThrThrArgArgAsnSerThrThrAsnGlyGluGluArgIle

PheSerLeuSerGlyAspAlaSerProSerArgProSerSerGlyAlaGlyThrAspGln

AlaValGlnGlnAlaHisPheLeuArgAspSerGluAspArgValHisGlySerSerGly

IleThrAsnGlnGlyAlaAlaAlaMetGlnGlnAlaValLeuSerAlaAlaArgGlyLeu

SerAspValSerHisAspAspSerAlaGlnThrGlnGlyAsnProThrValThrProLeu

ValSerAlaGlnAsnArgGlyProGluThrHisGlyLysGlyThrArg

PCR Amplification of Ats-1 cDNA

Ats-1 Colony PCR in NovaBlue *E. coli*

Ats-1 Colony PCR in BL21 *E. coli*

Purification of Recombinant Ats-1 : Coomassie-Stained SDS-PAGE Gel

Coomassie stained SDS-PAGE gels     Ats-1 =

Ni-NTA Column Purification of Recombinant Ats-1: Western Blot Detection

Western Blot (His-tag antibody) 8min exp.    Ats-1 = 48.6kDa

Depiction of the Sandwich ELISA using recombinant Ats-1 for IgG and IgM antibody detection.

IgG ELISA Using Recombinant Ats-1

IgG ELISA Using Recombinant Ats-1

Figure 13

IgG ELISA Using Recombinant Ats-1

Sample Size:
Positives: 28
Negatives: 31

| | |
|---|---|
| True Positives: | 27 |
| False Positives: | 6 |
| Positive Predictive Value: | 81.8% |
| True Negatives: | 25 |
| False Negatives: | 1 |
| Negative Predictive Value: | 96.2% |

IgM ELISA Using Recombinant Ats-1

IgM ELISA Using Recombinant Ats-1

Figure 16

IgM ELISA Using Recombinant Ats-1

| Sample Size: | True Positives: | 17 |
|---|---|---|
| Positives: 17 | False Positives: | 7 |
| Negatives: 29 | Positive Predictive Value: | 70.8% |
| | True Negatives: | 22 |
| | False Negatives: | 0 |
| | Negative Predictive Value: | 100% |

SEQUENCE LISTING

<160> NUMBER OF SEQ ID NOS: 24

<210> SEQ ID NO 1
<211> LENGTH: 1131
<212> TYPE: DNA
<213> ORGANISM: Anaplasma phagocytophilum

<400> SEQUENCE: 1

```
atgctaataa gaagaattct gactacatct aggaacgtcg ctgcgcgcat tgtttctgga     60
ttcacagctc cagccactga aaatactagc gcgagaacct caagaaatct cttaggtaca    120
acaggaaatt tctttaatgg cctcatgggt aaaggaaagc ctttttacca tcgcgcttct    180
gagatgcaga atctcccctg ggataaagag aggggcacaa aaataagttc gcactatgct    240
caaacagggc agttggtact gcaaattggc gatggaaggg tatctgaagg cgccttacag    300
atgttagaag cactggataa tagtgacgta ggagaactag atccaagtag taaaggttta    360
aatccaggaa tggatattgg cgccagaatg gatcataacc gagctaaaaa cgagtgtggt    420
gcgcttttag atcttagaaa aaagctggaa gaaacaggtg gtaagatttc cgtagagcgc    480
acaggcgacg gcttcactag aatgctagtg ataaaaatag acacaaaaaa taaatcagag    540
gaagaggtag aaaaagaagt acaactggta ctgggcactc taggtgttgg aagtaaaata    600
ctggccaagt ccattgctaa agagctaatg caccaagcaa aaacaaaaga tatgaatgct    660
cttgctccag taagccatac tcctcctgca caatcaaaac ctgacagtga tattcaagaa    720
aatagtgaaa aatctgcatc agcagacgct aaaaatagat ctcaggcacc tgatcaagaa    780
gaaaattcac cccgtgatac aacccgcaga aactctacta caaatggaga agaacgcatt    840
ttctcattga gcggagatgc gtcacctagc agaccttctt caggtgcagg caccgatcag    900
gccgttcagc aagcacactt cctaagagac tcagaggatc gtgtgcatgg cagcagcggt    960
atcaccaacc aaggagcagc ggctatgcaa caagcggtgc tttctgctgc tagaggacta   1020
agcgatgttt ctcatgatga ttcagcacaa acacaaggga atcctactgt cactcccttta  1080 gtaagcgcac agaatagagg cccagaaaca catggtaaag gtacgaggta a            1131
```

<210> SEQ ID NO 2
<211> LENGTH: 376
<212> TYPE: PRT
<213> ORGANISM: Anaplasma phagocytophilum

<400> SEQUENCE: 2

```
Met Leu Ile Arg Arg Ile Leu Thr Thr Ser Arg Asn Val Ala Ala Arg
 1               5                  10                  15
```

```
Ile Val Ser Gly Phe Thr Ala Pro Ala Thr Glu Asn Thr Ser Ala Arg
         20                  25                  30

Thr Ser Arg Asn Leu Leu Gly Thr Gly Asn Phe Phe Asn Gly Leu
     35                  40                  45

Met Gly Lys Gly Lys Pro Phe Tyr His Arg Ala Ser Glu Met Gln Asn
 50                  55                  60

Leu Pro Trp Asp Lys Glu Arg Gly Thr Lys Ile Ser Ser His Tyr Ala
 65                  70                  75                  80

Gln Thr Gly Gln Leu Val Leu Gln Ile Gly Asp Gly Arg Val Ser Glu
                 85                  90                  95

Gly Ala Leu Gln Met Leu Glu Ala Leu Asp Asn Ser Asp Val Gly Glu
                100                 105                 110

Leu Asp Pro Ser Ser Lys Gly Leu Asn Pro Gly Met Asp Ile Gly Ala
                115                 120                 125

Arg Met Asp His Asn Arg Ala Lys Asn Glu Cys Gly Ala Leu Leu Asp
            130                 135                 140

Leu Arg Lys Lys Leu Glu Glu Thr Gly Gly Lys Ile Ser Val Glu Arg
145                 150                 155                 160

Thr Gly Asp Gly Phe Thr Arg Met Leu Val Ile Lys Ile Asp Thr Lys
                165                 170                 175

Asn Lys Ser Glu Glu Glu Val Glu Lys Glu Val Gln Leu Val Leu Gly
                180                 185                 190

Thr Leu Gly Val Gly Ser Lys Ile Leu Ala Lys Ser Ile Ala Lys Glu
            195                 200                 205

Leu Met His Gln Ala Lys Thr Lys Asp Met Asn Ala Leu Ala Pro Val
    210                 215                 220

Ser His Thr Pro Pro Ala Gln Ser Lys Pro Asp Ser Asp Ile Gln Glu
225                 230                 235                 240

Asn Ser Glu Lys Ser Ala Ser Ala Asp Ala Lys Asn Arg Ser Gln Ala
                245                 250                 255

Pro Asp Gln Glu Glu Asn Ser Pro Arg Asp Thr Arg Arg Asn Ser
                260                 265                 270

Thr Thr Asn Gly Glu Glu Arg Ile Phe Ser Leu Ser Gly Asp Ala Ser
            275                 280                 285

Pro Ser Arg Pro Ser Ser Gly Ala Gly Thr Asp Gln Ala Val Gln Gln
    290                 295                 300

Ala His Phe Leu Arg Asp Ser Glu Asp Arg Val His Gly Ser Ser Gly
305                 310                 315                 320

Ile Thr Asn Gln Gly Ala Ala Ala Met Gln Gln Ala Val Leu Ser Ala
                325                 330                 335

Ala Arg Gly Leu Ser Asp Val Ser His Asp Asp Ser Ala Gln Thr Gln
            340                 345                 350

Gly Asn Pro Thr Val Thr Pro Leu Val Ser Ala Gln Asn Arg Gly Pro
    355                 360                 365

Glu Thr His Gly Lys Gly Thr Arg
    370                 375

<210> SEQ ID NO 3
<211> LENGTH: 33
<212> TYPE: DNA
<213> ORGANISM: Anaplasma phagocytophilum
<220> FEATURE:
<223> OTHER INFORMATION: Primer

<400> SEQUENCE: 3
gacgacgaca agatgtctgg tagtgtaaaa gcg                              33
```

<210> SEQ ID NO 4
<211> LENGTH: 38
<212> TYPE: DNA
<213> ORGANISM: Anaplasma phagocytophilum
<220> FEATURE:
<223> OTHER INFORMATION: Primer

<400> SEQUENCE: 4
gaggagaagc ccggtctaca tcacatcata ggaattag                                38

<210> SEQ ID NO 5
<211> LENGTH: 36
<212> TYPE: DNA
<213> ORGANISM: Anaplasma phagocytophilum
<220> FEATURE:
<223> OTHER INFORMATION: Primer

<400> SEQUENCE: 5
gacgacgaca agatgttaaa gctaggttgg tcttcg                                  36

<210> SEQ ID NO 6
<211> LENGTH: 36
<212> TYPE: DNA
<213> ORGANISM: Anaplasma phagocytophilum
<220> FEATURE:
<223> OTHER INFORMATION: Primer

<400> SEQUENCE: 6
gaggagaagc ccggtctatg catttttcac cctttg                                  36

<210> SEQ ID NO 7
<211> LENGTH: 36
<212> TYPE: DNA
<213> ORGANISM: Anaplasma phagocytophilum
<220> FEATURE:
<223> OTHER INFORMATION: Primer

<400> SEQUENCE: 7
gacgacgaca agatgcatag ggtagcaagg gcattg                                  36

<210> SEQ ID NO 8
<211> LENGTH: 36
<212> TYPE: DNA
<213> ORGANISM: Anaplasma phagocytophilum
<220> FEATURE:
<223> OTHER INFORMATION: Primer

<400> SEQUENCE: 8
gaggagaagc ccggtctaac tctgaccacc ttttcc                                  36

<210> SEQ ID NO 9
<211> LENGTH: 34
<212> TYPE: DNA
<213> ORGANISM: Anaplasma phagocytophilum
<220> FEATURE:
<223> OTHER INFORMATION: Primer

<400> SEQUENCE: 9
gacgacgaca agatggtatt ggatatgttt ggtc                                    34

<210> SEQ ID NO 10
<211> LENGTH: 33
<212> TYPE: DNA
<213> ORGANISM: Anaplasma phagocytophilum
<220> FEATURE:
<223> OTHER INFORMATION: Primer

<400> SEQUENCE: 10
gaggagaagc ccggtttata gaaattcatc atc 33

<210> SEQ ID NO 11
<211> LENGTH: 40
<212> TYPE: DNA
<213> ORGANISM: Anaplasma phagocytophilum
<220> FEATURE:
<223> OTHER INFORMATION: Primer

<400> SEQUENCE: 11
gacgacgaca agatgatgaa tttctataaa aatttttatg 40

<210> SEQ ID NO 12
<211> LENGTH: 34
<212> TYPE: DNA
<213> ORGANISM: Anaplasma phagocytophilum
<220> FEATURE:
<223> OTHER INFORMATION: Primer

<400> SEQUENCE: 12
gaggagaagc ccggtctaac taagagcctg attc 34

<210> SEQ ID NO 13
<211> LENGTH: 35
<212> TYPE: DNA
<213> ORGANISM: Anaplasma phagocytophilum
<220> FEATURE:
<223> OTHER INFORMATION: Primer

<400> SEQUENCE: 13
gacgacgaca agatggctga cgaaataagg ggttc 35

<210> SEQ ID NO 14
<211> LENGTH: 33
<212> TYPE: DNA
<213> ORGANISM: Anaplasma phagocytophilum
<220> FEATURE:
<223> OTHER INFORMATION: Primer

<400> SEQUENCE: 14
gaggagaagc ccggtctacc tcaccgcatc acg 33

<210> SEQ ID NO 15
<211> LENGTH: 37
<212> TYPE: DNA
<213> ORGANISM: Anaplasma phagocytophilum
<220> FEATURE:
<223> OTHER INFORMATION: Primer

<400> SEQUENCE: 15
gacgacgaca agatgactgg gggtggtgca gctttag 37

<210> SEQ ID NO 16
<211> LENGTH: 46
<212> TYPE: DNA
<213> ORGANISM: Anaplasma phagocytophilum
<220> FEATURE:
<223> OTHER INFORMATION: Primer

<400> SEQUENCE: 16
gaggagaagc ccggtttact tattaccctc tgaacactta gtgaac 46

<210> SEQ ID NO 17
<211> LENGTH: 35

```
<212> TYPE: DNA
<213> ORGANISM: Anaplasma phagocytophilum
<220> FEATURE:
<223> OTHER INFORMATION: Primer

<400> SEQUENCE: 17
gacgacgaca agatgcatag ttccaatcat atacg                              35

<210> SEQ ID NO 18
<211> LENGTH: 35
<212> TYPE: DNA
<213> ORGANISM: Anaplasma phagocytophilum
<220> FEATURE:
<223> OTHER INFORMATION: Primer

<400> SEQUENCE: 18
gaggagaagc ccggtctact ttagtcttcc gttac                              35

<210> SEQ ID NO 19
<211> LENGTH: 32
<212> TYPE: DNA
<213> ORGANISM: Anaplasma phagocytophilum
<220> FEATURE:
<223> OTHER INFORMATION: Primer

<400> SEQUENCE: 19
gacgacgaca agatggtgca gttttctttg cc                                 32

<210> SEQ ID NO 20
<211> LENGTH: 37
<212> TYPE: DNA
<213> ORGANISM: Anaplasma phagocytophilum
<220> FEATURE:
<223> OTHER INFORMATION: Primer

<400> SEQUENCE: 20
gaggagaagc ccggtctaga gctccaatcc ttttatc                            37

<210> SEQ ID NO 21
<211> LENGTH: 34
<212> TYPE: DNA
<213> ORGANISM: Anaplasma phagocytophilum
<220> FEATURE:
<223> OTHER INFORMATION: Primer

<400> SEQUENCE: 21
gacgacgaca agatgggtgc tggagttttt gaag                               34

<210> SEQ ID NO 22
<211> LENGTH: 39
<212> TYPE: DNA
<213> ORGANISM: Anaplasma phagocytophilum
<220> FEATURE:
<223> OTHER INFORMATION: Primer

<400> SEQUENCE: 22
gaggagaagc ccggttcagc aagcagtatt cctattcac                          39

<210> SEQ ID NO 23
<211> LENGTH: 34
<212> TYPE: DNA
<213> ORGANISM: Anaplasma phagocytophilum
<220> FEATURE:
<223> OTHER INFORMATION: Primer

<400> SEQUENCE: 23
gacgacgaca agatgctaag gctcatggtg atgg                               34
```

```
<210> SEQ ID NO 24
<211> LENGTH: 36
<212> TYPE: DNA
<213> ORGANISM: Anaplasma phagocytophilum
<220> FEATURE:
<223> OTHER INFORMATION: Primer

<400> SEQUENCE: 24
gaggagaagc ccggttcaaa aacgtattgt gcgacg                                36
```

ANAPLASMA TRANSLOCATED SUBSTRATE-1 (ATS-1) AND SERO-DETECTION OF ANAPLASMA PHAGOCYTOPHILUM

CROSS-REFERENCE TO RELATED APPLICATION

This application claims the benefit under 35 U.S.C. §119 (e) to U.S. Provisional Application No. 61/399,639 filed Jul. 15, 2010, the content of which is incorporated by reference herein in its entirety.

FIELD OF THE INVENTION

The present invention generally relates to the field of diagnostic assays for the detection of infectious agents in a mammal, including humans. Particular embodiments disclosed herein encompass Ats-1 protein that is useful in the sero-detection of *Anaplasma phagocytophilum*.

BACKGROUND OF THE INVENTION

*Anaplasma phagocytophilum* is a tick-borne pathogen responsible for granulocytic anaplasmosis in humans (Bakken J. S., et al.: Human granulocytic ehrlichiosis in the upper Midwest United States. A new species emerging? *JAMA* 272: 212-218, 1994). There has been a steady rise in cases of *Anaplasma* infections, alone or through co-infection with other tick-borne pathogens (Varde S., et al.: Prevalence of tick-borne pathogens in *Ixodes scapularis* in a rural New Jersey County. *Emerg. Infect. Dis.* 4: 97-99, 1998). Left unchecked, *Anaplasma* infection can be a potentially fatal disease resulting from the targeting and replication of the *Anaplasma* pathogen within human neutrophils (Bakken J. S. et al.: *JAMA* 272: 212-218, 1994). *Anaplasma phagocytophilum* infection thus emerges as a significant healthcare concern.

Detection of *Anaplasma* infection is crucial. Ideally, a diagnostic assay should be capable of detecting *Anaplasma* infection at its early stages, when antibiotic treatment is most effective and beneficial. Traditional detection methods for *Anaplasma* infection includes: (i) microscopic identification of morulae in granulocytes, (ii) PCR analysis using whole blood, (iii) isolation of the *Anaplasma* bacterium from whole blood, and (iv) serological tests, particularly indirect immunofluorescence assay (IFA). Microscopic examination is tedious and prone to sampling error. PCR test is sensitive in detecting the tick-borne pathogen during the period of time when the pathogen is present in the blood of infected patients. IFA is most commonly used (Park, J., et al.: Detection of antibodies to *Anaplasma phagocytophilum* and *Ehrlichia chaffeensis* antigens in sera of Korean patients by western immunoblotting and indirect immunofluorescence assays. *Clinical and Diagnostic Laboratory Immunology* 10(6): 1059-1064, 2003), but this test often gives false positive results. Such results can be attributed in part to the use of whole-cell antigens because such proteins may be shared with other bacteria (Magnarelli, L. A., et al.: Use of recombinant antigens of *Borrelia burgdorferi* and *Anaplasma phagocytophilum* in enzyme-linked immunosorbent assays to detect antibodies in white-tailed deer. *J. Wildlife Dis.* 40(2): 249-258, 2004). When clinical symptoms are manifested or high and stable antibody titers to *Anaplasma phagocytophilum* are found in patient blood, it reaches a late infection stage and bypasses the window of antibiotic treatment.

So far, there are only a few surface proteins on *Anaplasma* pathogen that are used in diagnostic assay for immuno-responses (i.e., IgG and IgM responses). It is generally believed that outer membrane proteins in pathogens are target for eliciting an immuno-response because they may be the first to be exposed to immune cells of a host. Regarding the *Anaplasma phagocytophilum* species, U.S. Pat. No. 6,964,855 discloses the use of an outer membrane protein and its fragments in a detection assay. U.S. Pat. No. 7,304,139 discloses a major surface protein 5 (MSP5) and its use in a diagnostic test. The '139 patent discloses a few patient's reactivity towards MSP5 and it lacks any data relating sensitivity and specificity, let alone any IgG/IgM distinction. Zhi et al. discloses cloning and expression of an outer membrane protein of 44 kDa and its use in a Western immunoblot assay (*J. Clinical Microbiology* 36(6): 1666-1673, 1998). Both MSP5 and p44 are outer membrane proteins in *Anaplasma phagocytophilum*.

The host immune response to tick-borne pathogen infection is frequently vigorous, and it is typically an easy task for investigators to identify many antigens (e.g., outer membrane proteins) which have been targeted as part of the host antibody response to infection. However, most of these antigens often fail when used as biomarkers for diagnostic purposes. Hence, it is well established that there is often no correlation between protein antigenicity, to the extent such a parameter can even be accurately predicted, and whether or not a given protein might serve as a useful diagnostic marker. It is the present inventors' contention that the proteins most beneficial as biomarkers for infection, and useful for assay development, are those that manage to evade the host immune response; successful identification of these specific antigens is a largely unmet challenge in the diagnostics industry, despite urgent needs for such biomarkers.

There remains a continuing need in the discovery of a novel antigen present in *Anaplasma phagocytophilum* that is useful and can provide a highly specific and sensitive test for sero-detection of this pathogen.

SUMMARY OF THE INVENTION

The present inventors unexpectedly discovered a diagnostic assay employing Ats-1 as an antigen to provide an accurate and sensitive diagnostic assay to detect *Anaplasma* infection. The finding is surprisingly because Ats-1 is an intracellular protein in *Anaplasma phagotycophilium* and is secreted by the bacteria during *Anaplasma* infection to weaken the host mitochondria.

The present invention provides an isolated protein of *Anaplasma phagocytophilum* that is useful in the detection of *Anaplasma phagocytophilum*. The isolated protein has an amino acid sequence of SEQ ID NO: 2. The present invention provides recombinant Ats-1 protein and methods of using the protein in the detection of recent or ongoing infections with *Anaplasma phagocytophilum*, which is useful in the diagnosis of human granulocytic anaplasmosis. The recombinant Ats-1 protein has an amino acid sequence of SEQ ID NO: 2.

In one aspect, the present invention provides a polypeptide having an amino acid sequence set forth in SEQ ID NO: 2.

In another aspect, the present invention provides a composition comprising the isolated Ats-1 protein and a support. Preferably, the support may be polyethylene, polypropylene and glass. Preferably, the support is a microtiter well.

In another aspect, the present invention provides an isolated polynucleotide with nucleotide sequence set forth in SEQ ID NO: 1.

In one aspect, the present invention provides a vector comprising the isolated polynucleotide of Ats-1. The vector may be pET. The vector may further comprise a promoter of DNA transcription operably linked to the isolated polynucleotides of interest. The vector may further comprise a promoter of DNA transcription operably linked to the isolated polynucleotides of interest. The vector may be pET, pENTR, or pCR®8/GW/TOPO®. The promoter may be a lac promoter, trp promoter or tac promoter.

In one aspect, the present invention provides a host cell comprising the vector. The host cell may be *E. coli*; which may include NovaBlue K12 strain or BL21 (DE3).

In one aspect, the present invention provides a method of preparing a recombinant protein of Ats-1 having an amino acid sequence of SEQ ID NO: 2. The method comprises the steps of (i) introducing the isolated Ats-1 gene into a host cell; (ii) growing the host cell in a culture under suitable conditions to permit production of said recombinant protein; and (iii) isolating the recombinant protein of Ats-1.

In one aspect, the present invention provides a method of detecting the presence of an antibody against *Anaplasma phagocytophilum* in a biological sample of a mammal, comprising: (i) immobilizing an isolated protein of Ats-1 onto a surface, the amino acid sequence of Ats-1 is set forth in SEQ ID NO: 2; (ii) contacting the isolated protein with a patient's biological sample, under conditions that allow formation of an antibody-antigen complex between the immobilized protein (antigen) and an antibody against *Anaplasma phagocytophilum*; and (iii) detecting the formation of the antibody-antigen complex; the detected antibody-antigen complex is indicative of the presence of said antibody against *Anaplasma phagocytophilum* in the biological sample.

In one aspect, the present invention provides a method of diagnosing an infection of *Anaplasma phagocytophilum* in a mammal, comprising the steps of (i) obtaining a biological sample from a mammal suspected of having an *Anaplasma phagocytophilum* infection; (ii) immobilizing an isolated Ats-1 protein onto a surface, wherein said isolated protein has an amino acid sequence set forth in SEQ ID NO: 2; (iii) contacting said isolated protein with said biological sample, under conditions that allow formation of an antibody-antigen complex; and (iv) detecting said antibody-antigen complex, wherein the presence of said detected antibody-antigen complex is indicative of an infection of *Anaplasma phagocytophilum* in said mammal.

In one aspect, the mammal is a human. In another aspect, ELISA test employs an IgG or IgM assay. Preferably, the IgG ELISA has a sensitivity of at least 90%, and a specificity of at least 80%. Preferably, the IgM ELISA has a sensitivity of at least 90%, and a specificity of at least 75%.

In yet another aspect, the present invention provides an article of manufacture comprising a packaging material and a recombinant Ats-1 protein. The article of manufacture may further comprise an instruction for detecting the presence of antibody against *Anaplasma phagocytophilum*.

BRIEF DESCRIPTION OF THE DRAWINGS

FIG. 1 depicts the nucleotide sequence of *Anaplasma* translocated substrate-1 (Ats-1) (NCBI Accession No. FJ210653) (SEQ ID NO:1).

FIG. 2 depicts the amino acid sequence of *Anaplasma* translocated substrate 1 (Ats-1) (NCBI Accession No. ACN39579) (SEQ ID NO:2).

FIG. 13 depicts the Positive Predictive Value (PPV) and Negative Predictive Value (NPV) of the IgG ELISA for Recombinant Ats-1 of *Anaplasma phagocytophilum*.

FIG. 16 depicts the Positive Predictive Value (PPV) and Negative Predictive Value (NPV) of the IgM ELISA for Recombinant Ats-1 of *Anaplasma phagocytophilum*.

DETAILED DESCRIPTION OF THE INVENTION

Figure 3:
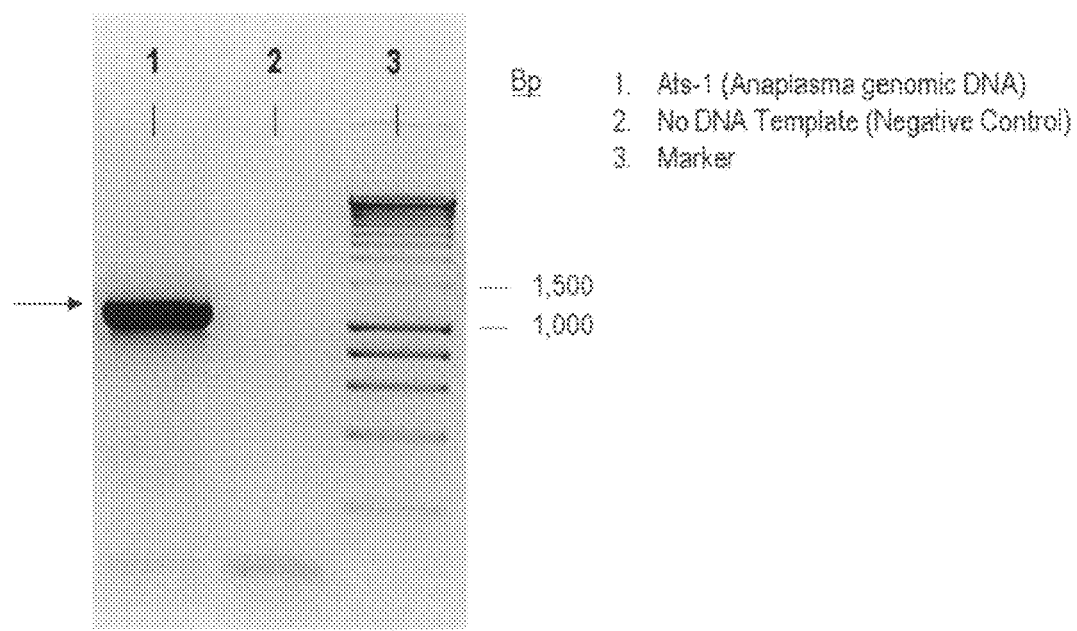
FIG. 3 depicts EK/LIC PCR amplification (from *Anaplasma* genomic DNA) of the cDNA encoding Ats-1 protein of *Anaplasma phagocytophilum*.
Figure 4:
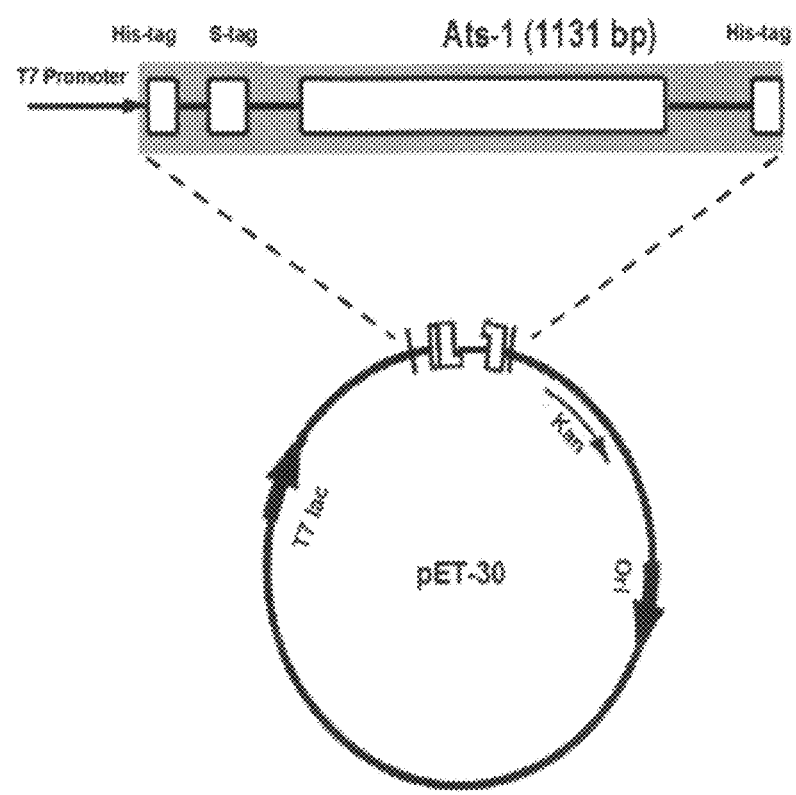
FIG. 4 depicts a pET-30 vector containing the Ats-1 gene.
Figure 5:
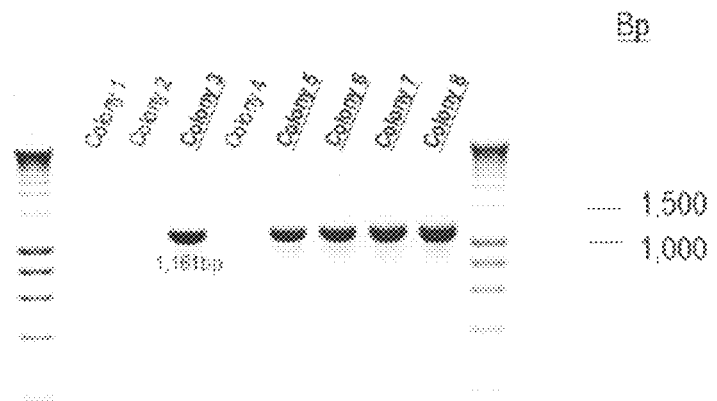
FIG. 5 depicts a colony PCR of transformants in NovaBlue *E. coli*.

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Various terms used throughout this specification shall have the definitions set out herein.

As used herein, "Ats-1" (*Anaplasma* translocated substrate-1) refers to a protein having an amino acid sequence as set forth in SEQ ID NO: 2 (NCBI Accession No. ACN39579). The protein is present in *Anaplasma phagocytophilum* and is encoded by a nucleotide sequence (NCBI Accession No. FJ210653). The Ats-1 protein is shown by the present inventors to bind to antibodies that are present in *Anaplasma* patients' sera in an ELISA assay.

As used herein, the term "ELISA" refers to "Enzyme-Linked ImmunoSorbent Assay" and is a biochemical technique used in detecting the presence of antibody or antigen in a sample.

As used herein, the term "IFA" refers to immunofluorescence assay. "IFA sero-positive sera from a patient" refers to sera (obtained from a patient) that exhibit positive immunofluorescence staining towards cells that have been infected with *Anaplasma phagocytophilum*. "IFA sero-negative sera from a patient" refers to sera (obtained from a patient) that exhibit negligible immunofluorescence staining towards cells that have been infected with *Anaplasma phagocytophilum*.

As used herein, the terms "protein," "polypeptide" or "peptide" are used interchangeably.

As used herein, the term "recombinant protein" refers to a protein that is recombinantly expressed by a host cell via the use of a vector that has been modified by the introduction of a heterologous nucleic acid. For purposes of the present invention, these proteins are intended to encompass some protein variations insofar as they retain the ability to bind to antibodies present in *Anaplasma* infected patients in an ELISA assay with comparable sensitivity and specificity. One of an ordinary skill in the art would appreciate that the protein variations may include (i) conservative substitutions, (ii) substitution, (iii) addition, and (iv) deletion of amino acids. It would be further appreciated that a protein variant, when having a sufficiently high % amino acid sequence identity (e.g., >95%) and a similar antibody binding activity as to the parent protein, is intended to be encompassed by the present invention.

As used herein, the term "detecting" is used in its broadest sense to include both qualitative and quantitative measurements. For example, one of the detecting method as described in this application is used to identify the presence of Ats-1 in a biological sample. However, the method can also be used to quantify the amount of Ats-1 in a biological sample and the quantity can be used to compare the Ats-1 levels from different biological samples.

As used herein, the term "detectable antibody" refers to an antibody that is capable of being detected either directly through a label amplified by a detection means, or indirectly through, e.g., another antibody that is labeled. For direct labeling, the antibody is typically conjugated to a moiety that is detectable by means such as a biotinylated antibody. Detection means refers to a moiety or technique used to detect the presence of the detectable antibody in the ELISA herein and includes detection agents that amplify the immobilized label such as label captured onto a microtiter plate. For example, the detection means is a fluorimetric detection agent such as avidin or streptavidin.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "primer" refers to a nucleotide sequence which can be extended by template-directed polymerization. For the purpose of this application, the term "nucleotide sequence" is intended to include DNA or modification thereof.

As used herein, the term "biological sample" may include but are not limited to blood (e.g., whole blood, blood serum, etc), cerebrospinal fluid, synovial fluid, and the like from a mammal such as a human or domestic animal. Extraction of nucleic acids from biological samples is known to those of skill in the art.

As used herein, the term "ROC" refers to Receiver Operating Characteristics Analysis. ROC analysis is a standard statistical tool for evaluation of clinical tests. ROC accesses the performance of the system in terms of "Sensitivity" and "1-Specificity" for each observed value of the discriminator variable assumed as decision threshold (i.e., cutoff value to differentiate between two groups of response). For ELISA, the cutoff value can be shifted over a range of observed values (i.e., $OD_{450/620}$ nm reading), and Sensitivity and 1-Specificity can be established for each of these values. The optimal pair of Sensitivity and Specificity is the point with the greatest distance in a Northwest direction.

In our earlier filed patent applications, the present inventors cloned, expressed, purified, and used recombinant type IV secretion system (TIVSS) proteins such as virB10 and virB11 (rTIVSS virB10 and rTIVSS virB11) and its protein fragments (Ser. No. 12/658,268 filed Feb. 9, 2010, now U.S. Pat. Nos. 8,323,907 and 12/658,506 filed Feb. 9, 2010 now U.S. Pat. No. 8,283,130) and hemolysin (Ser. No. 12/658,537 filed Feb. 9, 2010 now U.S. Pat. No. 8,257,938) in the development of a diagnostic ELISA test useful for detecting IgM/IgG antibody responses to *Anaplasma phagocytophilum*. The discovered assays discriminate between *Anaplasma phagocytophilum* IFA-positive and IFA-negative patient samples with high sensitivity (generally >70%) and specificity (generally >90%) values. The disclosure of these applications is hereby incorporated by reference in its entireties.

The present invention provides an isolated Ats-1 protein and its preparation thereof. The isolated Ats-1, when assayed in an ELISA assay, reacts to IFA sero-positive sera, indicating the presence of anti-Ats-1 antibody in patient sera infected with *Anaplasma phagocytophilum*. The specificity of this response is revealed by the fact that isolated Ats-1 does not react to IFA sero-negative sera from a patient infected with *Anaplasma phagocytophilum*.

Biology of ATS-1

*Anaplasma phagocytophilum*, the causative agent of human granulocytic anaplasmosis, is known to infect human neutrophils and inhibit mitochondria-mediated apoptosis. Specific bacterial factors involved in this process have remained largely unknown. In a recent study by Niu et al. (2010), a genomic DNA library of *Anaplasma phagocytophilum* was screened for effectors of the type IV secretion system by a bacterial two hybrid system. Using *Anaplasma phagocytophilum* VirD4 as bait, Niu identified a putative effector, named *Anaplasma* translocated substrate 1 (Ats-1). Using triple immunofluorescence labeling and Western blot analysis of infected cells, including human neutrophils, these authors determined that Ats-1 is abundantly expressed by *Anaplasma phagocytophilum*, translocated across the inclusion membrane, localized in the host cell mitochondria, and cleaved ectopically. These investigators showed that expressed Ats-1 targeted mitochondria in an N-terminal 17 residue-dependent manner, localized in matrix or at the inner membrane, and was cleaved as native protein, which required residues 55-57. In vitro-translated Ats-1 was imported in a receptor dependent manner into isolated mitochondria. Ats-1 inhibited etoposide-induced cytochrome c release from mitochondria, PARP cleavage, and apoptosis in mammalian cells, as well as Bax-induced yeast apoptosis. Ats-1(55-57) had significantly reduced anti-apoptotic activity. Bax redistribution was inhibited in both etoposide-induced and Bax-induced apoptosis by Ats-1. Taken together, Ats-1 is believed to represent a bacterial protein that traverses five membranes and prevents apoptosis at the mitochondria.

Ats-1 is a cytoplasmic protein in *Anaplasma*, and remains such throughout the early stages of infection as it is translocated through the type IV secretion system pilus to its final destination within the host mitochondria. As Ats-1 remains cytoplasmically-bound, it is predicted to be a poor antigen, if at all, by a host. In other word, Ats-1 is not expected to be seen by the host immune system during *Anaplasma* infection. The present inventors made a surprising discovery that Ats-1 is an optimal usefulness biomarker for early and late stage *Anaplasma* infection.

Recombinant Polypeptide of Ats-1

The present invention specifically contemplates expression and preparation of recombinant and synthetic polypeptides, characterized by being capable of binding to antibodies present in IFA positive patient sera. The recombinant Ats-1 has an amino acid sequence as set forth in SEQ ID NO: 2. In one embodiment, the present invention thus comprises the isolated nucleic acid having the nucleotide sequence set forth in FIG. 1 (SEQ ID NO: 1). For purposes of this application, it is intended to encompass other nucleotide sequences that exhibit nucleotide degeneracy but produce the same amino sequence of Ats-1. The recombinant proteins of Ats-1 expressed by the nucleic acids described herein encompasses the protein set forth in FIG. 2 (SEQ ID NO: 2). The recombinant Ats-1 protein described herein possesses the ability to bind to antibodies present in IFA positive sera (and not IFA negative sera).

It is understood that these recombinant polypeptides encompass variants. One type of variants includes modification of amino acids of recombinant polypeptides; such as, for example, substitution, deletion, or addition of amino acids. The present invention is intended to encompass the polypeptide variants of Ats-1 that retain the antibody binding ability towards IFA sero-positive sera and do not react to IFA sero-negative sera from *Anaplasma* infected patients. One of ordinary skill in the art would recognize that conservative amino acid substitutions may include simply substituting glutamic acid with aspartic acid; substituting isoleucine with leucine; substituting glycine or valine, or any divergent amino acid, with alanine, substituting arginine or lysine with histidine, and substituting tyrosine and/or phenylalanine with tryptophan. In another embodiment, addition and deletion of single amino acid may be employed. It is also appreciated by one of ordinary skill in the art that a few amino acids can be included or deleted from each or both ends, or from the interior of the polypeptide without significantly altering the peptide's ability to bind antibody (i.e., maintain high sensitivity and specificity (>90%), when tested in an ELISA assay.

Recombinant Expression of Ats-1 Polypeptides: Vectors and Hosts

Transcriptional and translational control sequences are DNA regulatory sequences, such as promoters, enhancers, terminators, and the like, that provide for the expression of a coding sequence in a host cell.

A DNA sequence is "operatively linked" or "operably linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

In one embodiment, the present invention provides the expression of the DNA sequences disclosed herein. As is well known in the art, DNA sequences may be recombinantly expressed by operatively linking the sequences to an expression control sequence in an appropriate expression vector; and expressing that linked vector via transformation in an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences. Suitable vectors include pET, pENTR, and pCR®8/GW/TOPO® and the like. The promoter contains lac promoter, trp promoter and tac promoter.

In one embodiment, a host cell contains the vector comprising the polynucleotides of the present invention. Exemplary host cell includes *E. coli*. Various *E. coli* strains include, for example, NovaBlue strain, BL21 (DE3) or BL21 pLsS (DE3).

It will be understood that not all vectors, expression control sequences and hosts will function equally well to express the DNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors, a person skilled in the art will be able to construct a variety of vector/expression control sequence/host combinations that will express the DNA sequences of this invention on fermentation or in large scale animal culture.

For recombinant expression of the various proteins used in this application, genes encoding the various proteins of interest can be conveniently inserted into a cloning vector and the vector containing the gene of interest is transfected or transformed into a suitable host cell for protein expression. Various publicly available vectors may be used. For example, vectors may include a plasmid, cosmid, viral particle, or phage. Examples of vectors included pET30, pENTR, pCR8/GW/TOPO® and the like. Vector components generally include, but are not limited to, one or more of a signal sequence, an origin of replication, a marker gene, an enhancer element, a promoter, and a transcription termination sequence. Construction of suitable vectors containing one or more of these components as well as the gene of interest employs standard ligation techniques which are known to the skilled artisan.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Examples of suitable selectable markers for mammalian cells include those that enable the identification of cells competent to take up the antigen-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 (Stinchcomb et al., *Nature,* 282:39 (1979). The trp1 gene provides a selection marker for a mutant strain of yeast lacking the ability to grow in tryptophan, for example, ATCC No. 44076 or PEP4-1 (Jones, *Genetics,* 85:12 (1977)).

A number of promoters can be used in order to enhance the expression of the gene of interest. In one embodiment, a promoter can be employed which will direct expression of a polynucleotide of the present invention in *E. coli*. Other equivalent transcription promoters from various sources are known to those of skill in the art. Exemplary promoters include the β-lactamase and lactose promoter systems (Chang et al., Nature, 275:615 (1978)), alkaline phosphatase, a tryptophan (trp) promoter system (Goeddel, *Nucleic Acids Res.,* 8:4057 (1980)), and the like.

A promoter may be operably linked to the protein-encoding nucleic acid sequence to direct mRNA synthesis. Promoters recognized by a variety of potential host cells are well known. For example, promoters for use in bacterial systems also will contain a Shine-Dalgarno (S.D.) sequence operably linked to the DNA encoding the protein of interest.

Transcription of a DNA encoding the antigen by higher eukaryotes may be increased by inserting an enhancer sequence into the vector. Enhancers are cis-acting elements of DNA, usually about from 10 to 300 bp, which can act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the 15-kDa coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding *Anaplasma phagocytophilum* antigen.

The nucleic acid (e.g., genomic DNA) encoding recombinant *Anaplasma phagocytophilum* antigen of the present invention may be inserted into a replicable vector for cloning (amplification of the DNA) or for expression. For example, a full-length Ats-1 gene may be inserted into a replicable vector for cloning and for expression of full-length Ats-1 protein or fragments thereof. The appropriate nucleic acid sequence may be inserted into the vector by a variety of procedures. In general, DNA is inserted into an appropriate restriction endonuclease site(s) using techniques known in the art.

Host cells are transfected or transformed with expression or cloning vectors described herein for antigen production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

Methods of eukaryotic cell transfection and prokaryotic cell transformation are known to the ordinarily skilled artisan, for example, $CaCl_2$, $Ca_2PO_4$, liposome-mediated and electroporation. Depending on the host cell used, transformation is performed using standard techniques appropriate to such cells. The calcium treatment employing calcium chloride, as described in Sambrook et al., or electroporation is generally used for prokaryotes. For mammalian cells without such cell walls, the calcium phosphate precipitation method of Graham and van der Eb, *Virology,* 52:456-457 (1978) can be employed. Transformations into yeast are typically carried out according to the method of Van Solingen et al., *J. Bact.,* 130:946 (1977). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, See Keown et al., Methods in Enzymology, 185:527-537 (1990). The particular selection of host/cloning vehicle combination may be made by those of skill in the art after due consideration of the principles set forth without departing from the scope of this invention (See, e.g., Sambrook et al., *Molecular Cloning, A Laboratory Manual* $2^{nd}$ edition, 1989, Cold Spring Harbor Press, NY).

The Ats-1 polypeptide (antigen) may be recombinantly produced as a fusion polypeptide with a heterologous polypeptide. The heterologous polypeptide may serve as a signal sequence or other polypeptide having a specific cleavage site at the N-terminus of the mature protein or polypeptide. In general, the signal sequence may be a component of the vector, or it may be a part of the antigen-encoding DNA that is inserted into the vector. In mammalian cell expression, mammalian signal sequences may be used to direct secretion of the protein, such as signal sequences from secreted polypeptides of the same or related species, as well as viral secretory leaders. An overview of expression of recombinant proteins is found in *Methods of Enzymology v.* 185, Goeddel, D. V. ed. Academic Press (1990).

Recombinant gene expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Recombinant gene expression, alternatively, may be measured by immunological methods, such as immunohistochemical staining of cells or tissue sections and assay of cell culture or body fluids, to quantitate directly the expression of gene product. Antibodies useful for immunohistochemical staining and assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to *Anaplasma phagocytophilum* DNA and encoding a specific antibody epitope.

After expression, recombinant antigen may be recovered from culture medium or from host cell lysates. If membrane-bound, it can be released from the membrane using a suitable detergent solution (e.g. Triton-X 100) or by enzymatic cleavage. Cells employed in expression of *Anaplasma phagocytophilum* antigen can be disrupted by various physical or chemical means, such as freeze-thaw cycling, sonication, mechanical disruption, or cell lysing agents.

It may be desired to purify recombinant antigen from host cell proteins. The following procedures are exemplary of suitable purification procedures: by fractionation on an ion-exchange column; reverse phase HPLC; chromatography on silica or on a cation-exchange resin such as DEAE; chromatofocusing; SDS-PAGE; ammonium sulfate precipitation; metal chelating columns to bind epitope-tagged forms of the protein of interest. Various methods of protein purification may be employed and such methods are known in the art and described for example in Deutscher, *Methods in Enzymology*, 182 (1990); Scopes, Protein Purification: Principles and Practice, Springer-Verlag, New York (1982). The purification step(s) selected will depend, for example, on the nature of the production process used and the particular antigen produced.

Other than recombinantly expressed, Ats-1 protein may be purified directly from cultured *Anaplasma phagocytophilum*. One skilled in the art would recognize culturing *Anaplasma phagocytophilum* using standard methods. One skilled in the art can also recognize methods to obtain purified Ats-1 protein from cultured *Anaplasma phagocytophilum*. To that end, cultured *Anaplasma phagocytophilum* may be pelleted using standard centrifugation (e.g., 10,000×g for 10 minutes). Pelleted cells can be disrupted by physical or chemical means, such as freeze-thaw cycling, sonication, mechanical disruption, or cell lysing agents (e.g., BugBuster® Master Mix reagent). Methods to purify Ats-1 protein from cultured cells are known in the art. Exemplary procedures include: fractionation on an ion-exchange column; reverse phase high performance liquid chromatography (HPLC); liquid chromatography-mass spectrometry (LC-MS); chromatography on silica or on a cation-exchange resin such as DEAE; chromatofocusing; SDS-PAGE; ammonium sulfate precipitation; immunoaffinity chromatography; immunoprecipitation; and the like. Various methods of protein isolation are described in Deutscher, *Methods in Enzymology*, 182 (1990); Scopes, Protein Purification: Principles and Practice, Springer-Verlag, New York (1982).

ELISA Assay

Detection of antibody binding in IFA sero-positive sera may be accomplished by techniques known in the art, e.g., ELISA (enzyme-linked immunosorbent assay), western blots, and the like. In one embodiment, antibody binding is assessed by detecting a label on the primary antibody. In another embodiment, the primary antibody is assessed by detecting binding of a secondary antibody or reagent to the primary antibody. In a further embodiment, the secondary antibody is labeled. Many means are known in the art for detecting binding in an immunoassay and are within the scope of the present invention. For example, to select specific epitopes of recombinant or synthetic polypeptide, one may assay antibody binding in an ELISA assay wherein the polypeptides or its fragments containing such epitope.

As appreciated by one skilled in the art, an enzyme-linked immunosorbent assay (ELISA) may be employed to detect antibody binding in IFA sero-positive sera. In an initial step of an ELISA, an antigen is immobilized onto a surface (for example by passive adsorption known as coating). For purposes of this application, exemplary antigens include *Anaplasma phagocytophilum* Ats-1 protein, succinate dehydrogenase and p44-8 outer membrane protein and the like. Recombinant or purified (i.e., isolated) full-length protein as well as fragments thereof may be used. Immobilization of antigen may be performed on any inert support that is useful in immunological assays. Examples of commonly used supports include small sheets, Sephadex and assay plates manufactured from polyethylene, polypropylene or polystyrene. In a preferred embodiment the immobilized antigens are coated on a microtiter plate that allows analysis of several samples at one time. More preferably, the microtiter plate is a microtest 96-well ELISA plate, such as those sold under the name Nunc Maxisorb or Immulon.

Antigen immobilization is often conducted in the presence of a buffer at an optimum time and temperature optimized by one skilled in the art. Suitable buffers should enhance immobilization without affecting the antigen binding properties. Sodium carbonate buffer (e.g., 50 mM, pH 9.6) is a representative suitable buffer, but others such as Tris-HCl buffer (20 mM, pH 8.5), phosphate-buffered saline (PBS) (10 mM, pH 7.2-7.4) are also used. Optimal coating buffer pH will be dependent on the antigen(s) being immobilized. Optimal results may be obtained when a buffer with pH value 1-2 units higher than the isoelectric point (pI) value of the protein is used. Incubation time ranges from 1-8 hours, overnight or 24 hours. Incubation may be performed at temperatures ranging from 4-37° C. Preferably, immobilization takes place overnight at 4° C. Preferably, Ats-1 is immobilized onto a surface (e.g., a microtiter plate) at 4° C. overnight (i.e., 16 hours). The plates may be stacked and coated long in advance of the assay itself, and then the assay can be carried out simultaneously on several samples in a manual, semi-automatic, or automatic fashion, such as by using robotics.

Blocking agents are used to eliminate non-specific binding sites in order to prevent unwanted binding of non-specific antibody to the plate. Examples of appropriate blocking agents include detergents (for example, Tween-20, Tween-80, Triton-X 100, sodium dodecyl sulfate), gelatin, bovine serum albumin (BSA), egg albumin, casein, non-fat dried milk and the like. Preferably, the blocking agent is casein. The blocking treatment typically takes place under conditions of ambient temperatures for about 0.5-4 hours, preferably 1 to 2 hours.

After coating and blocking, the plate is washed with TBST (0.05% Tween-20) and the protein is dried on the plate using a vacuum drier in 37° C. for about 1 to 4 hours, preferably 2-3 hours. The plates are then covered with plate sealers, and put in a dark sealer pouch and sealed with a humidity sponge also in it. This can be stored in 4° C. for a few months, depending on the stability of the protein.

Sera from the control (IFA sero-negative) or IFA sero-positive patients are added to the immobilized antigens in the plate. Biological sample (i.e., sera) may be diluted in buffer. For IgM detection, human sera may be diluted with casein dilution buffer at 1:50 to 1:400 dilutions. Preferably, human sera are diluted at 1:100. For IgG detection, human sera may be diluted with casein dilution buffer at 1:50 to 1:400 dilutions. Preferably, human sera are at 1:200. 5% Casein in 1× Phosphate Buffered Saline (PBS) containing 0.05% TWEEN 20® detergent may be used. TWEEN 20® acts as a detergent to reduce non-specific binding.

The conditions for incubation of the biological sample and immobilized antigen are selected to maximize sensitivity of the assay and to minimize dissociation. Preferably, the incubation is accomplished at a constant temperature, ranging from about 0° C. to about 40° C., preferably from about 22 to 25° C. to obtain a less variable, lower coefficient of variant (CV) than at, for example, room temperature. The time for incubation depends primarily on the temperature, being generally no greater than about 10 hours to avoid an insensitive assay. Preferably, the incubation time is from about 0.5 to 3 hours. More preferably, the incubation time is 1-2 hours. Optimal time of 1 hour at room temperature is found to maximize binding to immobilized capture antigen.

Following incubation of the biological sample and immobilized antigen, unbound biological sample is separated from the immobilized antigen by washing. The solution used for washing is generally a buffer ("washing buffer") with a pH determined using the considerations and buffers described above for the incubation step, with a preferable pH range of about 6-9. Preferably, pH is 7. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step.

Next, the immobilized capture antigen and biological sample are contacted with a detectable antibody at a time and temperature optimized by one skilled in the art. Detectable antibody may include a monoclonal antibody or a polyclonal antibody. These antibodies may be directly or indirectly conjugated to a label. Suitable labels include moieties that may be detected directly, such as fluorochrome, radioactive labels, and enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, horseradish peroxidase (HRP), alkaline phosphatase (AP), glucose oxidase (GO), and the like. Preferably, the detection antibody is a goat anti-human IgG polyclonal antibody that binds to human IgG and is directly conjugated to HRP. Incubation time ranges from 30 minutes to overnight, preferably about 60 minutes. Incubation temperature ranges from about 20-40° C., preferably about 22-25° C., with the temperature and time for contacting the two being dependent on the detection means employed.

The conjugation of such labels to the antibody, including the enzymes, is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Because IgG may occasionally interfere in IgM detection assays, IgG in patient sera may be removed prior to IgM ELISA. One of ordinary skill in the art would appreciate various methods of IgG removal from biological samples (e.g., human sera). For example, commercial reagents such as GullSORB™ (Meridian Bioscience, Inc., Cincinnati, Ohio) may be used. IgG may also be removed using Aurum Serum Protein Mini Kit (Bio-Rad, Hercules, Calif.), sucrose gradient sedimentation and the like. Preferably, IgG is removed using GullSORB®. Ideally, an anti-human IgG antibody is used to neutralize the IgG in human sera. The method for IgG removal can be conveniently optimized by one of ordinary skill in the art. For example, human sera can be incubated with anti-human IgG antibody prior to the IgM ELISA assay.

Diagnostic Kits Employing Recombinant Ats-1 Polypeptides

The present invention provides a kit for the diagnosis of *Anaplasma* infection. In one embodiment, the kit is an ELISA kit containing recombinant polypeptides described herein, detection reagents including primary or secondary antibodies, and other necessary reagents including enzyme substrates and color reagents. Additional components that may be present within such kits include an instruction detailing the detection procedure for *Anaplasma phagocytophilum*, using the recombinant polypeptides of the present invention. The diagnostic kit of the present invention further comprises a positive and negative serum control. The diagnostic kit of the present invention can also be used in diagnosing other infectious diseases involving *Anaplasma phagocytophilum* such as Human Granulocytic Anaplasmosis (HGA).

The following Examples are offered by way of illustration and not by way of limitation.

EXPERIMENTAL STUDIES

Example 1

Ats-1 in *Anaplasma phagocytophilum*

Using a genomic DNA library of *Anaplasma phagocytophilum* and a bacterial two-hybrid system, Niu et al. has recently disclosed a functional role for Ats-1 (~48 kd bacterial protein). Immunofluorescence study reveals that Ats-1 can be translocated across multiple membranes into mitochondria of the host cells (e.g., neutrophils). Upon arrival in mitochondria, Ats-1 is shown to inhibit etoposide-induced cytochrome C release, PARP cleavage, and apoptosis. These authors proposed that Ats-1 represents a bacterial protein that traverses through cellular membranes and prevents apoptosis of the host cells in their mitochondria.

The present inventors surprisingly discovered a novel and unrelated role for Ats-1. We presented herein that Ats-1 is a good biomarker for detecting *Anaplasma* infection in human, and for diagnosing *Anaplasma* infection. Evidence is presented herein to demonstrate that recombinantly expressed Ats-1, when immobilized on a surface (e.g., in an ELISA assay), represents a good detection biomarker for both IgG and IgM antibody responses to *Anaplasma phagocytophilum* infection.

Example 2

Cloning and Recombinant Expression of Ats-1 and Six (6) Cytoplasmic Proteins in *Anaplasma phagocytophilum*

(i) PCR Amplification and Ligation into Plasmid Vector

To determine if Ats-1 protein may contain an epitope for antibody recognition, we cloned and recombinantly expressed Ats-1 protein in *Anaplasma phagocytophilum*.

Our cloning strategy involves designing and preparing synthetic oligonucleotides (~30 bp in length) and used them to amplify the cDNA that encodes the Ats-1 protein. For comparison purposes, we successfully cloned six (6) additional cytoplasmic proteins: including hemolysin, outer membrane protein (p44), and type IV secretion system proteins (i.e., VirB9, VirB10, VirB11, and VirD4) in *Anaplasma phagocytophilum*.

To this end, genomic DNA of *Anaplasma phagocytophilum* (a generous gift from Dr. S. Dumler at Johns Hopkins University) was used as the template for each of the PCR reactions. Synthetic oligonucleotides corresponding to eleven (11) genes were used for the PCR amplification reactions (See, Table 2). Using these synthetic oligonucleotides to amplify cDNAs from genomic *Anaplasma phagocytophilum* DNA, we successfully amplified nine (9) of the genes; namely, p44, virB3, virB6, virB9, virB10, virB11, virD4, succinate dehydrogenase and hemolysin; but failed to amplify two (2) genes (namely, virB4 and virB8) (See, Table 2).

Of the nine (9) amplified genes (Table 2), three (3) genes (namely, virB3, virB6 and succinate dehydrogenase iron-sulfur subunit) failed to express any recombinant proteins. Accordingly, in our hands, we were able to amplify six (6) genes (that are related to type IV secretion system) and recombinantly express the respective proteins (Table 2).

Table 1 summarizes the nucleotide sequence accession numbers of the six (6) genes used in our PCR amplification reaction. The IgG and IgM responses of the recombinant proteins (prepared using the respective six (6) genes) when used in ELISA are also shown (Table 1).

FIG. 3 shows an agarose gel of the amplified Ats-1 gene prior to processing of the PCR reaction in preparation for ligation into pET30 vector. The amplicon having an expected size (~1.16 kb) is shown by the arrow in this figure. In preparation for ligation with the vector, the PCR amplification reactions were treated to remove any remaining nucleotides, primers, and reaction components. The resulting PCR products were then treated with T4 DNA polymerase and ligated into pET30 using standard protocols (See, FIG. 4). Ligation of insert DNA (including, e.g., virB3, virB6, virB9, virB10, virB11, virD4, succinate dehydrogenase iron-sulfur, hemolysin and p44 proteins) was performed as described below.

T4 Polymerase Treatment of PCR Products and Ligation into pET30 Vector

In order to ligate the cloned insert DNA with the plasmid vector, it is necessary to create compatible ends between the amplicon and the chosen vector (e.g., pET30 Ek/LIC). We generated overhangs compatible with the Ek/LIC cloning vector on the insert DNA by T4 DNA polymerase treatment of the PCR amplicon. We ligated the treated amplicon into the expression vector to form pET30/insert DNA.

FIG. 4 depicts the pET30 vector containing the inserted gene (e.g., full-length virB3, virB6, virB9, virB10, virB11, virD4, succinate dehydrogenase iron-sulfur, hemolysin and p44). The nucleotide sequences of virB3, virB6, virB9, virB10, virB11, virD4, succinate dehydrogenase iron-sulfur, hemolysin and p44 are publicly available and their accession numbers are listed in Table 2.

Transformation of Recombinant Clones into NovaBlue *E. coli*

In these series of experiments, we transformed the ligated DNAs (annealing reaction) into host bacterial cells (NovaBlue *E. coli*). The ligated DNAs included virB3, virB6, virB9, virB10, virB11, virD4 amplicons as well as succinate dehydrogenase iron-sulfur, hemolysin and p44 amplicons. We chose NovaBlue *E. coli* because this bacterial strain is optimized for producing a stable cell line containing a recombinant insert (see, NovaBlue Ek/LIC manual). Transformation into NovaBlue competent *E. coli* (Novagen) was performed using standard protocols. First, appropriate numbers of 20 μl aliquots of competent cells were prepared from −80° C., and allowed to thaw on ice for several minutes, followed by the addition of 1 μl of the annealing reaction and gentle stirring. The mixture was further incubated on ice for an additional 5 minutes, followed by heating the tubes for 30 seconds in a 42° C. water bath. The tubes were immediately placed on ice for 2 minutes. SOC (Super Optimal broth with Catabolite repression medium, containing 2% w/v bacto-tryptone, 0.5% w/v bacto-yeast extract, 10 mM NaCl, 2.5 mM KCl, 10 mM $MgCl_2$, 20 mM glucose) (at room temperature) was added into the tubes, and the reactions were further incubated for 1 hour at 37° C. with shaking (250 rpm). Cells were plated onto LB agar plates (containing kanamycin) and incubated at 37° C. overnight.

Colony PCR of NovaBlue Transformants

To confirm the successful transformation of insert DNA (pET30/insert DNA) in *E. coli* cells, we selected several colonies of each transformant grown on LB plates (with kanamycin), and performed colony PCR using the same set of Ek/LIC primers as in the amplification of the genes from the *Anaplasma* genomic DNA. An aliquot of each PCR reaction was analyzed using agarose gel electrophoresis.

As an example, FIG. 5 shows agarose gel electrophoresis analysis of eight of Ats-1 transformants in NovaBlue *E. coli*. Amplicons of expected size (~1,161 bp) were observed following analysis of the PCR reactions. NovaBlue *E. coli* colonies containing the pET30/insert DNA were further cultured in LB-kanamycin broth (for the isolation of plasmids).

Plasmid Mini-Preps

In order to confirm the presence and sequence accuracy of the cloned insert DNA in the pET30 vector, we performed sequence analysis on the recombinant plasmids. The sequence analysis also provides information that the insert was in-frame of the upstream His-tag sequence. First, we isolated plasmid DNA from the transformed *E. coli*. Wizard Plus SV Minipreps DNA Purification system (Promega) was used according to the manufacturer's recommended protocol. The concentration (1 $OD_{260/280}$=0.5 mg/ml) and the relative purity ($OD_{260/280}$) of the isolated plasmid DNA preparations were determined by spectrophotometric analysis.

Sequencing Analysis of Insert DNA

We next performed sequence analysis on the isolated plasmid DNA using the Applied BioSystems 3130 Genetic Analyzer DNA Sequencing instrument. All of the insert DNA were confirmed to be accurate by BLAST analysis and in-frame. BLAST (Basic Local Alignment Search Tool) analysis of the sequences confirmed a match between each of the nucleotide sequences and the published sequences of the respective *Anaplasma phagocytophilum* genes.

Transformation of BL21 (DE3) *E. coli* with Recombinant Plasmids

After confirmation of the obtained recombinant plasmids, we proceeded to transform them into BL21 (DE3) competent *E. coli* (Novagen). Transformation was carried out by removing the appropriate number of 20 μl aliquots of competent cells from −80° C., allowing the tubes to thaw on ice for several minutes, followed by the addition of 1 μl of the plasmid preparation to the cells with gentle stirring. The mixture was incubated on ice for 5 minutes, followed by heating of the tubes for exactly 30 seconds in a 42° C. water bath. The tubes were immediately placed on ice for 2 min. SOC (room temperature) was added, and the reactions were further incubated at 37° C. for 1 hour at 250 rpm. Cells were then plated onto LB agar plated (containing kanamycin) and incubated at 37° C. overnight.

Colony PCR of BL21 (DE3) Transformants

To confirm the successful transformation of recombinant pET30/insert DNA in BL21 (DE3) *E. coli* cells, we selected several colonies of each transformant grown on LB plates (with kanamycin), and performed colony PCR using forward and reverse vector-specific primers. An aliquot of each PCR reaction was analyzed using agarose gel electrophoresis.

Figure 6:
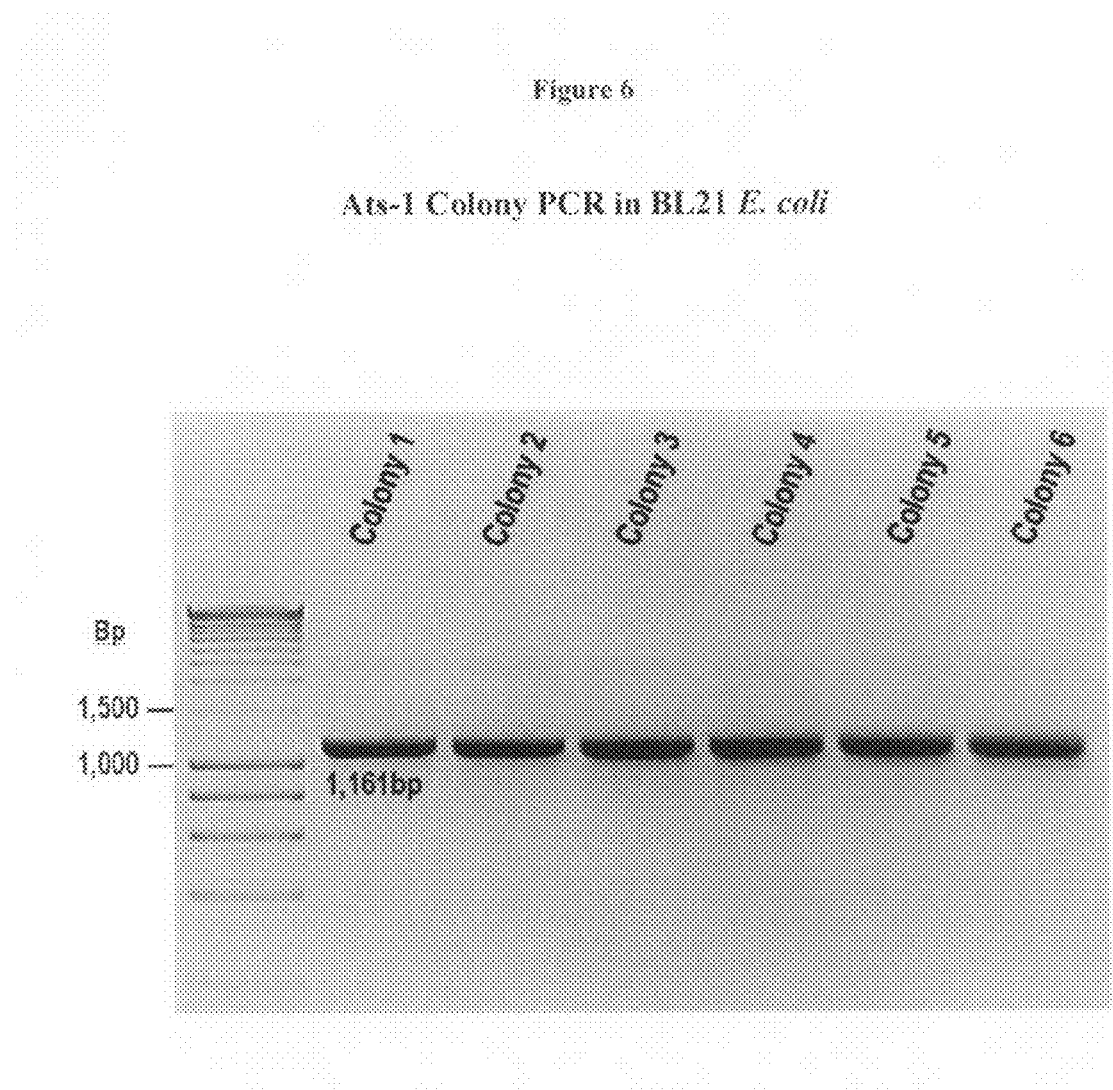
FIG. 6 depicts a colony PCR of transformants in BL21 (DE3) *E. Coli*
Figure 7:
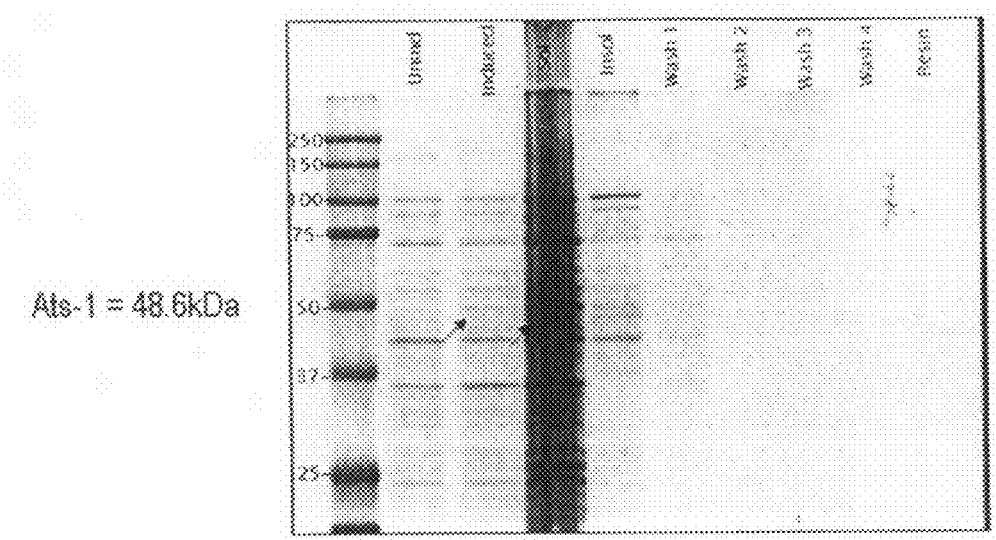
FIG. 7 depicts a Coomassie-stained SDS PAGE gel showing the recombinant expression of Ats-1 protein.
Figure 8:
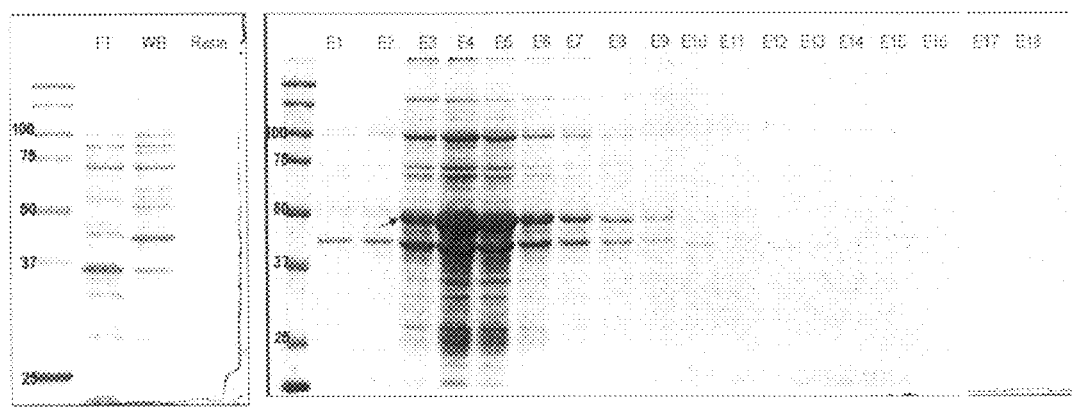
FIG. 8 depicts a Coomassie-stained SDS PAGE gel showing the Ni-NTA column purification of recombinant Ats-1 protein.
Figure 9:
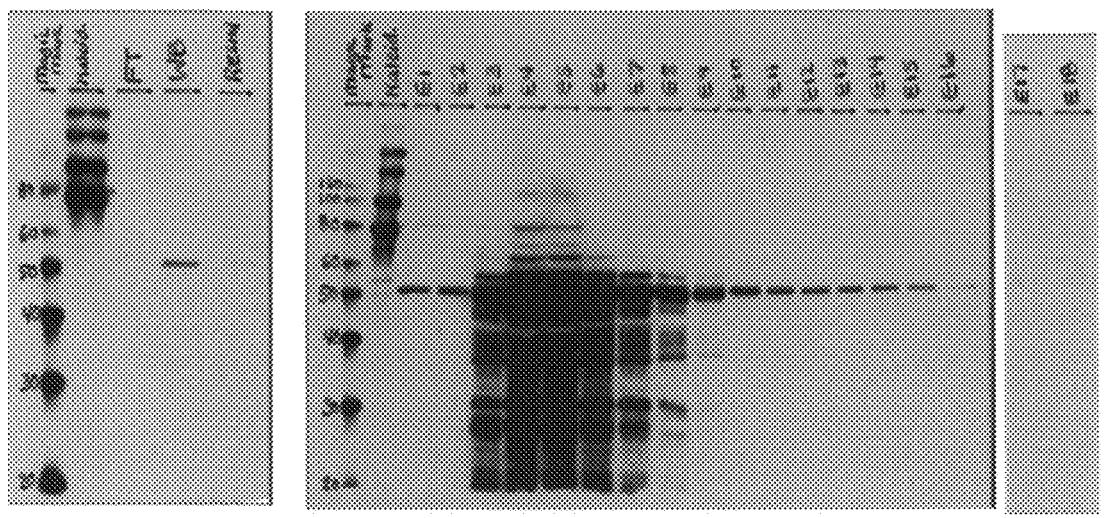
FIG. 9 depicts Western blot detection with monoclonal anti-His tag antibody of His-tag labeled recombinant Ats-1.
Figure 10:
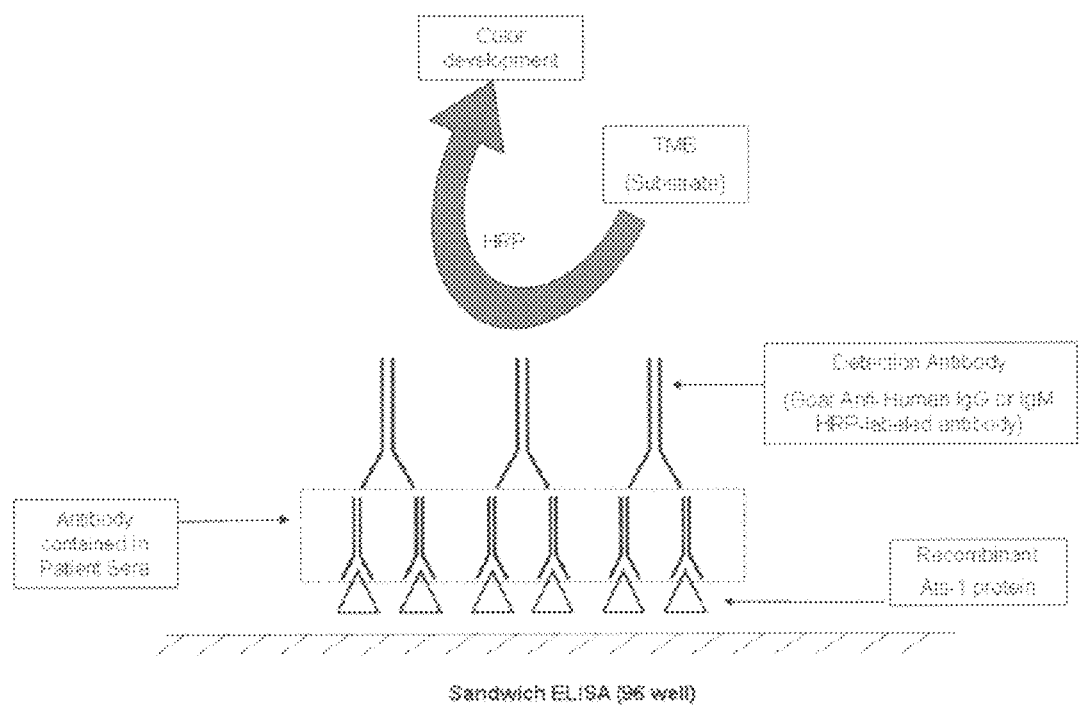
FIG. 10 is a schematic depiction of the Sandwich ELISA using recombinant Ats-1 for IgG and IgM antibody detection.
Figure 11:
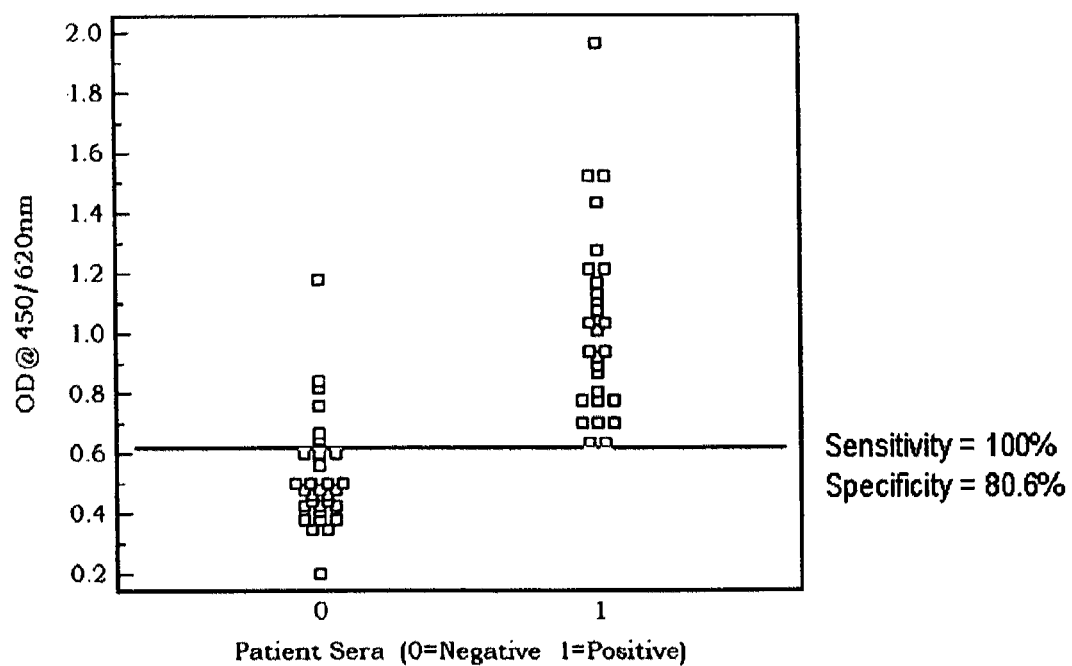
FIG. 11 depicts an IgG ELISA data using recombinant Ats-1 of *Anaplasma phagocytophilum*.
Figure 12:
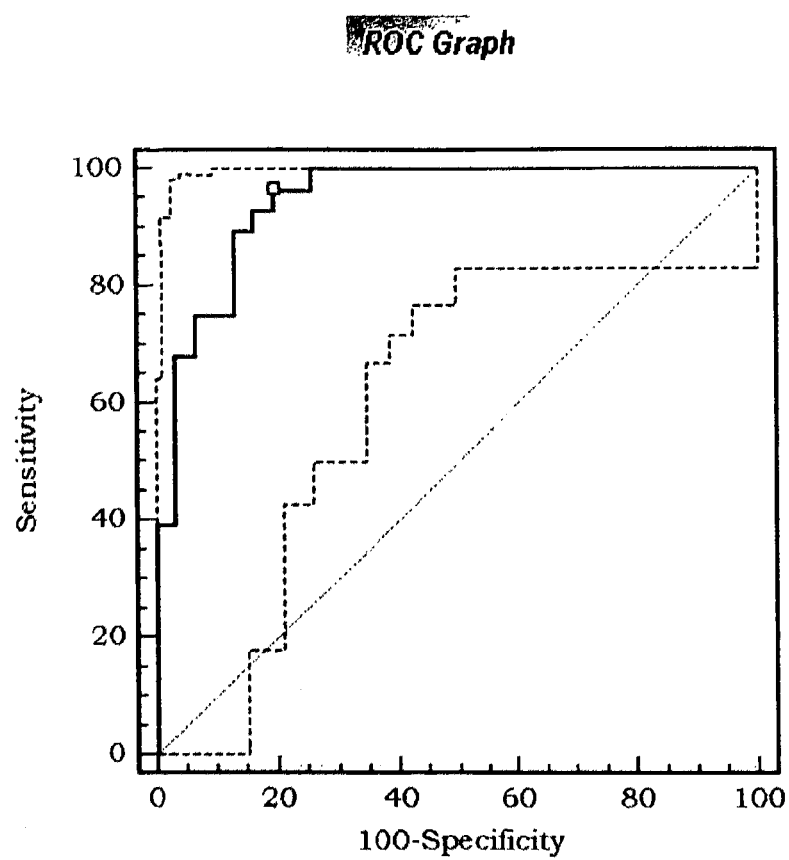
FIG. 12 depicts a ROC analysis for recombinant Ats-1 IgG ELISA.

FIG. 6 shows agarose gel electrophoresis analysis of six (6) of Ats-1 transformants in BL21 (DE3) *E. coli*. Amplicons of expected size (~1,161 bp) were observed following analysis of the PCR reactions. Several BL21 (DE3) *E. coli* colonies containing the pET30/insert DNA were then processed for recombinant expression.

Isolation and Purification of Recombinant Ats-1

Figure 14:
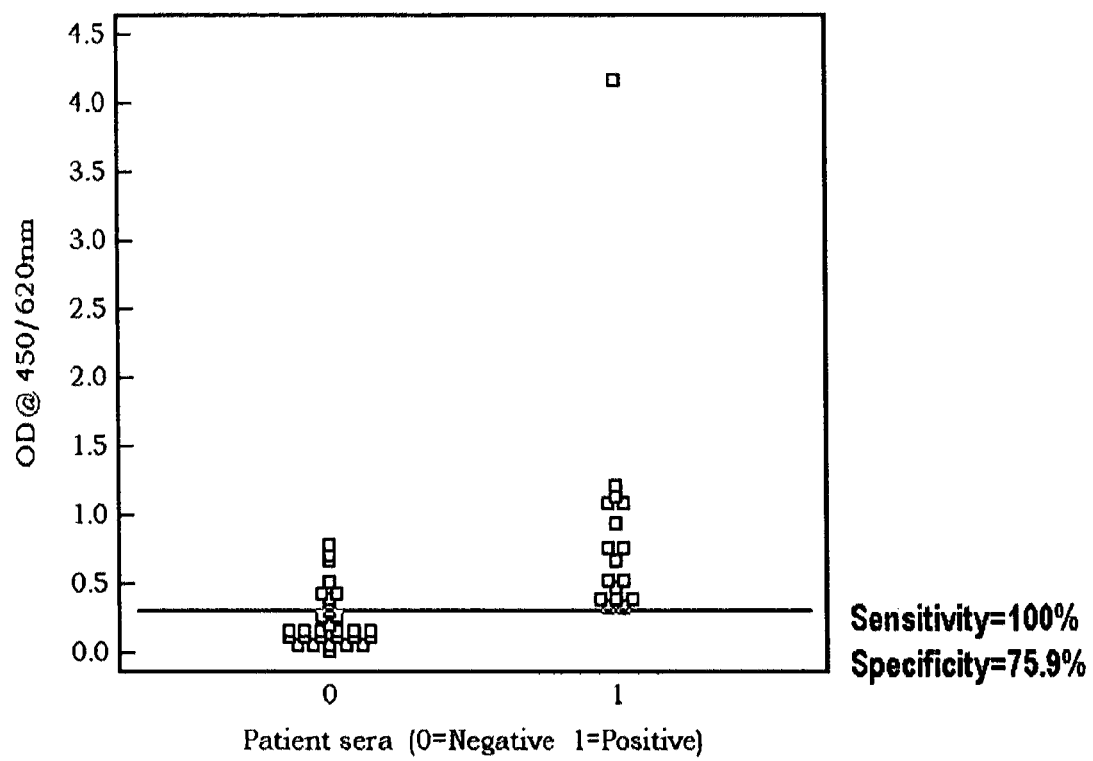
FIG. 14 depicts an IgM ELISA data using recombinant Ats-1 of *Anaplasma phagocytophilum*.

Isolation of the expressed recombinant Ats-1 was performed using BugBuster Master Mix (Novagen) according to the manufacturer's protocol. After IPTG induction, bacterial cells were harvested from liquid cultures by centrifugation at 3,000 rpm for 15 minutes. Recombinant non-TIVSS protein was isolated both from supernatant and cell pellets. Cell pellets were re-suspended in 5 ml of BugBuster Master Mix (Novagen) by gentle vortexing. The resulting cell suspensions were incubated on a rotating mixer for 20 minutes at room temperature. The mixtures were centrifuged at 4° C. for 20 minutes at 16,000×g to remove the insoluble cellular debris. The supernatant was transferred to a fresh tube for SDS PAGE analysis (See, FIG. 7).

The supernatant was then processed to isolate the soluble fraction. Soluble fraction purification was carried out by using Ni-NTA Buffer kit (Novagen) according to the manufacturer's protocol. An aliquot of the purified inclusion body fraction was analyzed on an SDS PAGE gel. (See, FIGS. 8 & 9).

In addition to Ats-1 we also confirmed the successful transformation of recombinant pET30/insert DNA for virB3, virB6, virB9, virB10, virB11, virD4, succinate dehydrogenase iron-sulfur, hemolysin and p44.

Expression of Various Recombinant Proteins

FIG. 13 depicts a flow chart depicting the steps for IPTG induction of recombinant TIVSS and non-TIVSS proteins in BL21 *E. coli*. For expression of various recombinant TIVSS (rTIVSS) proteins (for example, virB3, virB6, virB9, virB10, virB11, and virD4) and non-TIVSS proteins (for example, succinate dehydrogenase iron-sulfur submit and p44), BL21 (DE3) *E. coli* were transformed with the pET30-rTIVSS plasmid DNA containing the respective genes.

The expression was induced with IPTG as follows: 3 ml of LB broth cultures with kanamycin (30 μg/ml final concentration) were inoculated with BL21 transformed with pET30-rTIVSS plasmid. Cultures were grown to mid-log phase ($OD_{600}$=0.5) at 37° C. with shaking at 250 rpm. When the cultures reached mid-log, the entire 3 ml was added to 100 ml LB broth with kanamycin (30 μg/ml final concentration) and allowed to grow to mid-late log phase ($OD_{600}$=0.5-1). When the cultures reached mid-late log stage, they were split into two separate 50 ml batches in 250 ml flasks. To one flask, 500 μl of IPTG was added (final concentration of 1 mM), this flask being the induced flask. No IPTG was added to the other flask which served as a control for assessing induction—the uninduced flask. Growth of the IPTG and control cultures was allowed to proceed for 4-4.5 hours at 37° C. with shaking (250 rpm). Cell pellets were then harvested by centrifugation at 3,000 rpm for 15 minutes at 4° C., and subsequently processed with BugBuster Master Mix (Novagen) as described below.

Recombinant Expression of virB3, virB6, and Succinate Dehydrogenase Iron-Sulfur Subunit Fail After IPTG induction and BugBuster Master Mix treatment, equal concentrations (~3 μg) of a soluble cytoplasmic and insoluble (inclusion body) fraction from IPTG-treated (induced) cells and control cells were analyzed on SDS-PAGE. SDS-gels were stained using Coomassie-blue. Induction of recombinant protein expression was considered to be successful when there was a marked increase (observed on SDS-PAGE protein gels) in the target protein expression in the IPTG-treated sample, as compared to that of the control cells (i.e., no IPTG).

FIG. 7 shows that IPTG induction of Ats-1 (soluble and inclusion body) before and after IPTG induction. Note that Ats-1 shows marked induction relative to the control (uninduced), and the induced Ats-1 is predominantly sequestered within the soluble fraction (see arrow).

Table 2 summarizes the results of recombinant expression of TIVSS and non-TIVSS proteins. Using our expression protocol, we found that virB3, virB6 and succinate dehydrogenase fail to express any recombinant protein.

Altogether, our results show that virB4 and virB8 genes could not be amplified under these experimental conditions. Unexpectedly, virB3 and virB6 failed to recombinantly express their corresponding proteins. We were successful in recombinantly express only four (4) of the eight (8) TIVSS protein components (namely, virB9, virB10, virB11, and virD4) in *Anaplasma phagocytophilum*. In addition, we were only able to recombinantly express p44 outer membrane protein and hemolysin, but not succinate dehydrogenase iron-sulfur subunit (See, Table 2).

Example 3

IgG/IgM ELISA for Recombinantly Expressed Ats-1 Protein

We adopted IgG and IgM ELISA assays and evaluated the binding activity of the recombinant proteins towards IgG and IgM. The ELISA procedure involves: (i) coating 96-well micro-titer plates with the recombinant protein at varying concentrations at 4° C. overnight; (ii) adding casein in PBS to block non-specific binding; (iii) drying plates and keeping them in 4° C. for long term storage; (iv) adding patients' sera to allow formation of antibody-antigen complex; (v) detecting the antibody-antigen complex. IFA sero-positive sera served as positive controls, and IFA sero-negative sera served as negative controls. Detection of antibody-antigen complex was performed with the use of horseradish peroxidase.

a) Patient Study: Ats-1 IgG ELISA

We conducted IgG ELISA tests for binding activity towards the recombinantly expressed Ats-1 protein. FIG. 10 shows a depiction of that sandwich ELISA.

We examined recombinant Ats-1 in an IgG ELISA. Recombinant Ats-1 was prepared using the cloning-expression method detailed above. When tested, we observed a dose-dependent increase in the binding activity (as measured by $OD_{450/620nm}$) towards IgG sero-positive sera (FIG. 11). The sensitivity of the IgG ELISA for recombinant Ats-1 was found to be 100%. The specificity of the IgG ELISA was 80.6% (See, FIG. 11). A threshold level of ≧70% is normally considered by industrial standard to be meaningful and acceptable for accurate interpretation of ELISA sensitivity or specificity.

Because Ats-1 provides adequate IgG ELISA, we analyzed ROC (area under the curve) using the raw IgG ELISA data with the MedCalc statistical software. FIG. 12 summarizes the performance analysis of the ROC curve. FIG. 13 shows the Positive Predictive Value (PPV) and the Negative Predictive Value (NPV) for the IgG ELISA using the recombinant Ats-1.

b) Patient Study: Ats-1 IgM ELISA

In this second series of studies, we examined recombinant Ats-1 in IgM ELISA. FIG. 10 shows a depiction of that sandwich ELISA. Recombinant Ats-1 protein exhibited a dose-dependent increase in binding towards IgM sero-positive serum (as measured by $OD_{450/620nm}$). IgM ELISA for recombinant Ats-1 attained a 100% sensitivity (FIG. 14) and 75.9% specificity, both of which satisfies the threshold ($\geqq$70%) required by industry.

Figure 15:
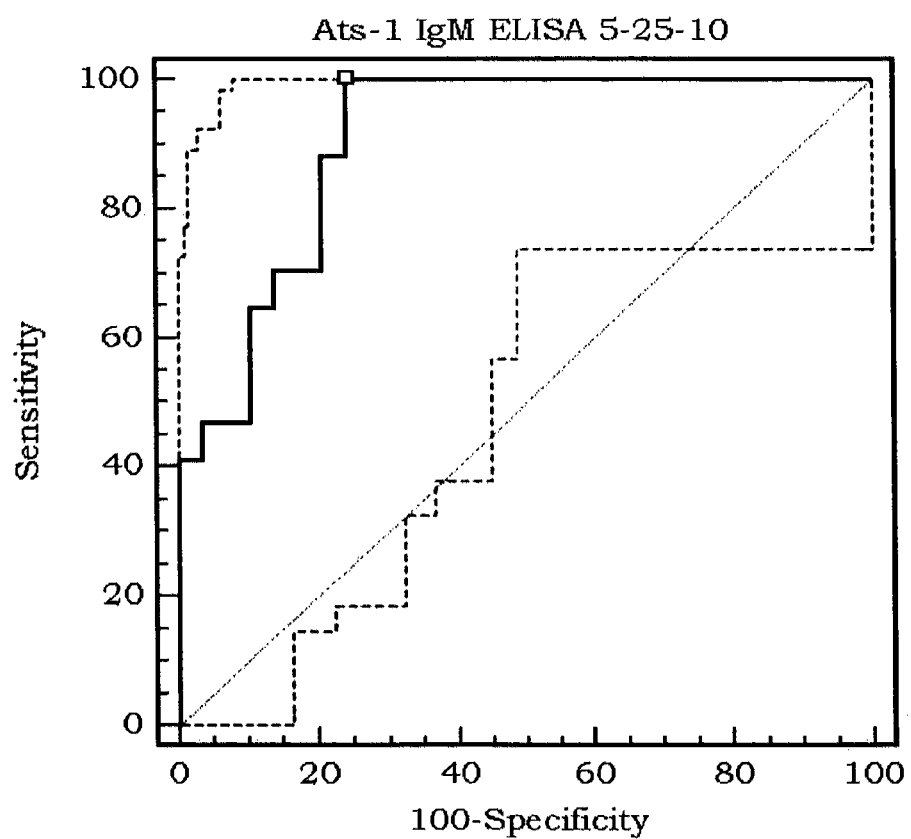
FIG. 15 depicts a ROC analysis for recombinant Ats-1 IgM ELISA.

The raw IgM ELISA data was analyzed with ROC curve determination using MedCalc statistical software. Performance analysis of ROC curve is shown in FIG. 15. FIG. 16 shows the Positive Predictive Value (PPV) and the Negative Predictive Value (NPV) for the IgM ELISA using the recombinant Ats-1.

Experimental Protocols

Induction and Purification of Ats-1:

1. Add a loop full of frozen stock of Ats-1 in BL21(DE3) cells in 3 ml LB-Kan 30 culture and incubate at 37° C. shaking at 250 rpm until $OD_{600}$ is approximately 0.5. Add the entire 3 ml culture to 100 ml LB-Kan medium in a 500 ml baffled flask.
2. Shake the culture in 37° C. incubator at 250 rpm until the $OD_{600}$ is approximately 0.5-1.0
3. After the desired OD has been reached, take an aliquot of the culture and label it "Uninduced".
4. Induce the culture by adding 1 ml of 100 mM IPTG and return to shake in 37° C. incubator at 250 rpm for 4 hours. After 4 hours, take an aliquot from the culture and label it "Induced". Analyze induced and uninduced samples on an SDS-PAGE gel to observe the expression of the protein
5. Harvest cells from induced culture by centrifugation at 10,000×g for 10 minutes using a weighed centrifuge tube. Decant the supernatant and allow the pellet to drain as much liquid as possible.
6. Resuspend the cell pellet in room temperature Bug-Buster® Master Mix reagent by pipetting or gentle vortex, using about 2.5 ml per 50 ml of culture.
7. Incubate the suspension on a shaking platform or rotating mixer at a slow setting at room temperature for 20 minutes.
8. Centrifuge the cell debris at 16,000×g for 20 minutes at 4° C. to separate soluble and insoluble fractions.
9. Transfer the supernatant (soluble fraction) to a fresh, sterile tube. Ats-1 is found in the soluble fraction.
10. Buffers in the Novagen Ni-NTA kit come as 4×. Dilute only necessary amounts using distilled water
11. Add resin to the binding buffer (equal to 1 ml resin for each 4 ml of soluble fraction)
12. Shake it for 5 min in 4° C. and let it settle for a few minutes on ice
13. Take out the binding buffer from the top previously added and add the soluble fraction. Let it shake in 4° C. for 1 hour
14. Pour in column, and slowly let flow through in tube on ice: "Flow Through"
15. When finished collecting flow through, add 2×4 ml of wash buffer and collect in tube on ice: "Wash Buffer1" and "Wash Buffer2"
16. When finished collecting wash buffer, add 0.6 ml of elution buffer 18 times and collect in 18×1.5 ml Eppendorf tubes: "Elutions 1-18"
17. Save some of the leftover resin (put in PBS) to run on gel along with the flow through, wash buffer, and elutions. Run gels in double (one gel stain with coomassie and use the other for western blot probed with a His-TAG antibody).
18. Combine the elutions that contain Ats-1. Buffer exchange it in PBS, and read the concentration of the protein

*Anaplasma* Ats-1 IgG ELISA

1. Antigen coating concentration 1.0 µg/ml in carbonate buffer (pH 9.6) (100 µl per well). Coating overnight in 4° C.
2. Wash three time in PBST buffer (0.05% Tween-20)
3. Block with 200 µl blocker buffer (casein in PBS, Thermo Sci. #37528). Incubate for 1 hour in room temperature
4. Wash three times with PBST buffer (0.05% Tween-20)
5. Add 100 µl 1:200 diluted human sera (dilution buffer: 1:20 casein buffer in PBST (0.05% Tween-20). Incubate for 1 hour in room temperature
6. Wash four times with PBST buffer (0.05% Tween-20)
7. Add goat anti-human IgG antibody (1:15,000 diluted in casein dilution buffer (1:20 casein buffer in PBST (0.5% Tween-20)). Incubate for 1 hour in room temperature
8. Wash four times with PBST buffer (0.05% Tween-20)
9. Add 100 µl TBM substrate. Incubate in room temperature for 5 minutes 10 seconds in the dark.
10. Stop the reaction with 0.5M $H_2SO_4$
11. Read the result at $OD_{450/620nm}$

*Anaplasma* Ats-1 IgM ELISA

1. Antigen coating concentration 0.5 µg/ml in carbonate buffer (pH 9.6) (100 µl per well). Coating overnight in 4° C.
2. Wash three time in PBST buffer (0.05% Tween-20)
3. Block with 200 µl blocker buffer (casein in PBS, Thermo Sci. #37528). Incubate for 1 hour in room temperature
4. Wash three times with PBST buffer (0.05% Tween-20)
5. Dilute human sera in GullSorb™ (1:10) to prepare mixture 1. Incubate in room temperature for 5 minutes. Dilute incubated mixture 1 in sample dilution buffer (1:20 casein buffer in PBST (0.5% Tween-20)). Therefore, the total dilution factor for human sera is 1:100
6. Add 100 µl 1:100 diluted human sera to the plate. Incubate for 1 hour in room temperature
7. Wash four times with PBST buffer (0.05% Tween-20)
8. Add goat anti-human IgM antibody (1:10,000 diluted in casein dilution buffer (1:20 casein buffer in PBST (0.5% Tween-20)). Incubate for 1 hour in room temperature
9. Wash four times with PBST buffer (0.05% Tween-20)
10. Add 100 µl TBM substrate. Incubate in room temperature for 5 minutes in the dark.
11. Stop the reaction with 0.5M $H_2SO_4$
12. Read the result at $OD_{450/620nm}$ All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Various modifications of the above-described modes for carrying out the invention that are obvious to those skilled in the filed of molecular biology, recombinant expression and related fields are intended to be within the scope of the following claims.

TABLE 1

|  | Accession number: | IgG ELISA | IgM ELISA |
|---|---|---|---|
| p44 | YP_504769 | (42 Samples) Sens: 42.9% Spec: 100% | Not tested |
| VirB9 | YP_505897 | Checkerboard - no conditions showed good differentiation | (42 Samples) Sens: 61.9% Spec: 100% |
| VirB10 | YP_505896 | (42 Samples) Sens: 81.0% Spec: 71.4% | (42 Samples) Sens: 71.4% Spec: 90.5% |
| VirB11 | YP_505895 | (42 Samples) Sens: 71.4% Spec: 76.2% | Not tested |
| VirD4 | YP_505894 | (42 Samples) Sens: 81.0% Spec: 42.9% | Not tested |
| Hemolysin | YP_504658 | (42 Samples) Sens: 81.0% Spec: 57.1% | (42 Samples) Sens: 76.2% Spec: 90.5% |

TABLE 2

Oligonucleotide Sequences Used in Gene Amplification for *Anaplasma phagocytophilum* Encoding TIVSS and Non-TIVSS Protein Components

| Recombinant TIVSS & Non-TIVSS Protein | NCBI Accession # | Oligonucleotides | Gene Amplification | Recombinant Expression |
|---|---|---|---|---|
| virB3 | YP_504978 | Fwd: 5'-gacgacgacaagatgtctggtagtgtaaaagcg-3' (Seq. ID No. 3)<br>Rev: 5'-gaggagaagcccggtctacatcacatcataggaattag-3' (Seq. ID No. 4) | Yes | No |
| virB4 | YP_504979 | Fwd: 5'-gacgacgacaagatgttaaagctaggttggtcttcg-3' (Seq. ID No. 5)<br>Rev: 5'-gaggagaagcccggtctatgcatttttcacccttg-3' (Seq. ID No. 6) | No | No |
| virB6 | YP_504980 | Fwd: 5'-gacgacgacaagatgcatagggtagcaagggcattg-3' (Seq. ID No. 7)<br>Rev: 5'-gaggagaagcccggtctaactctgaccaccttttcc-3' (Seq. ID No. 8) | Yes | No |
| virB8 | YP_505898 | Fwd: 5'-gacgacgacaagatggtattggatatgtttggtc-3' (Seq. ID No. 9)<br>Rev: 5;40 -gaggagaagcccggtttatagaaattcatcatc-3' (Seq. ID No. 10) | No | No |
| virB9 | YP_505897 | Fwd: 5'-gacgacgacaagatgatgaatttctataaaaatttttatg-3' (Seq. ID No. 11)<br>Rev: 5'-gaggagaagcccggtctaactaagagcctgattc-3' (Seq. ID No. 12) | Yes | Yes |
| virB10 | YP_505896 | Fwd: 5'-gacgacgacaagatggctgacgaaataaggggttc-3' (Seq. ID No. 13)<br>Rev: 5'-gaggagaagcccggtctacctcaccgcatcacg-3' (Seq. ID No. 14) | Yes | Yes |
| virB11 | YP_505895 | Fwd: 5'-gacgacgacaagatgactgggggtggtgcagctttag-3' (Seq. ID No. 15)<br>Rev: 5'-gaggagaagcccggtttacttattaccctctgaacacttagtgaac-3' (Seq. ID No. 16) | Yes | Yes |
| virD4 | YP_505894 | Fwd: 5'-gacgacgacaagatgcatagttccaatcatatacg-3' (Seq. ID No. 17)<br>Rev: 5'-gaggagaagcccggtctactttagtcttccgttac-3' (Seq. ID No. 18) | Yes | Yes |
| Succinate Dehydrogenase, iron-sulfur subunit | YP_504786 | Fwd: 5'-gacgacgacaagatggtgcagttttctttgcc-3' (Seq. ID No. 19)<br>Rev: 5'-gaggagaagcccggtctagagctccaatccttttatc-3' (Seq. ID No. 20) | Yes | No |
| Hemolysin | YP_504658 | Fwd: 5'-gacgacgacaagatgggtgctggagtttttgaag-3' (SEQ ID No. 21)<br>Rev: 5'-gaggagaagcccggttcagcaagcagtattcctattcac-3' (SEQ ID No. 22) | Yes | Yes |

TABLE 2-continued Oligonucleotide Sequences Used in Gene Amplification for *Anaplasma phagocytophilum* Encoding TIVSS and Non-TIVSS Protein Components

| Recombinant TIVSS & Non-TIVSS Protein | NCBI Accession # | Oligonucleotides | Gene Amplification | Recombinant Expression |
|---|---|---|---|---|
| p44-8 Outer Membrane Protein | YP_504769 | Fwd: 5'-gacgacgacaagatgctaaggctcatggtgatgg-3' (Seq. ID No. 23)<br>Rev: 5'-gaggagaagcccggttcaaaaacgtattgtgcgacg-3' (Seq. ID No. 24) | Yes | Yes |

What is claimed is:

1. A method of detecting the presence of an anti-*Anaplasma* translocated substrate-1 (Ats-1) antibody against *Anaplasma phagocytophilum* in a biological sample of a patient suspected of having an infection of *Anaplasma phagocytophilum*, comprising the steps of:
   (i) immobilizing an isolated Ats-1 protein antigen onto a surface of a support;
   (ii) contacting said immobilized Ats-1 protein with a biological sample from a patient suspected of containing an anti-Ats-1 antibody against *Anaplasma phagocytophilum*, under conditions that allow formation of a complex of the antibody and the protein antigen; and
   (iii) detecting the formation of said antibody-protein antigen complex,
   wherein said detected antibody-protein antigen complex is indicative of the presence of said anti-Ats-1 antibody against *Anaplasma phagocytophilum* in said biological sample of said patient.

2. The method of claim 1, wherein said isolated Ats-1 protein is a recombinant protein.

3. The method of claim 1, wherein said support is selected from the group consisting of polyethylene, polypropylene and glass.

4. The method of claim 1, wherein said support is a microtiter well.

5. The method of claim 1, wherein said biological sample is whole blood.

6. The method of claim 1, wherein said antibody is an IgG.

7. The method of claim 1, wherein said antibody is an IgM.

8. The method of claim 1, wherein said method is an ELISA.

9. The method of claim 8, wherein said ELISA has a sensitivity of at least 90%.

10. The method of claim 8, wherein said ELISA has a specificity of at least 75%.

11. A method of diagnosing an infection of *Anaplasma phagocytophilum* in a patient by detecting the presence of an anti-Ats-1 antibody, comprising the steps of:
    (i) obtaining a biological sample from a patient suspected of having an anti-Ats-1 antibody against *Anaplasma phagocytophilum;*
    (ii) immobilizing an isolated Ats-1 protein antigen onto a surface of a support;
    (iii) contacting said immobilized Ats-1 protein with said biological sample, under conditions that allow formation of a complex of the antibody and the protein antigen;
    and
    (iv) detecting said antibody-protein antigen complex,
    wherein the presence of said detected antibody-protein antigen complex is indicative that said patient has an infection of *Anaplasma phagocytophilum.*

12. The method of claim 11, wherein said isolated Ats-1 protein is a recombinant protein.

13. The method of claim 11, wherein said support is selected from the group consisting of polyethylene, polypropylene and glass.

14. The method of claim 11, wherein said support is a microtiter well.

15. The method of claim 11, wherein said biological sample is whole blood.

16. The method of claim 11, wherein said antibody is IgG.

17. The method of claim 11, wherein said antibody is an IgM.

18. The method of claim 11, wherein said method is an ELISA.

19. The method of claim 18, wherein said ELISA has a sensitivity of at least 90%.

20. The method of claim 18, wherein said ELISA has a specificity of at least 75%.

* * * * *